US008617888B2

United States Patent
Jin et al.

(10) Patent No.: US 8,617,888 B2
(45) Date of Patent: Dec. 31, 2013

(54) BACTERIAL MEDIATED DELIVERY OF NUCLEAR PROTEIN INTO PLURIPOTENT AND DIFFERENTIATED CELLS

(75) Inventors: Shouguang Jin, Gainesville, FL (US); Candace Bichsel, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 213 days.

(21) Appl. No.: 12/842,448

(22) Filed: Jul. 23, 2010

(65) Prior Publication Data
US 2012/0021517 A1 Jan. 26, 2012

(51) Int. Cl.
C12N 5/00 (2006.01)
C12N 5/02 (2006.01)
C07H 21/04 (2006.01)
C07K 1/00 (2006.01)
C07K 14/00 (2006.01)
C07K 17/00 (2006.01)

(52) U.S. Cl.
USPC .......................... 435/377; 536/23.5; 530/350

(58) Field of Classification Search
USPC .......................... 435/377; 536/23.5; 530/350
See application file for complete search history.

(56) References Cited

PUBLICATIONS

Vance et al., Infection and Immunity, 73(3): 1706-1713, 2005.*
Loessner et al., Expert. Opin. Biol. Ther., 4(2): 157-168, 2004.*
Frey et al., Vaccine, 25: 5598-5605, 2008.*
Silby et al., FEMS Microbial Review, 35: 652-680, 2011.*
Oliveri et al. Regenerative Medicine, 2(5): 795-816, Sep. 2007.*
Sullivan et al. Reproductive BioMed. Online, 16(1): 41-50, Nov. 2008.*
Djuric and Ellis, 202, Stem Cell Research and Therapy, 2010,1:3.*
Huangfu et al, 2008, Nature Biotechnology, 26:795-7.*
Plath et al. Nature Reviews, 12: 253-265, 2011.*
Brizzard et al., Current Protocols in Neuroscience, 5.8.1-5.8.10, 1997.*
Gerecht-Nir, Developmental Dynamics, 232: 487-497 (2005).*
Yu, J. et al. "Human Embryonic Stem Cells Reprogram Myeloid Precursors Following Cell-Cell Fusion" *Stem Cells*, 2006, pp. 168-176, vol. 24.
Takahashi, K. et al. "Induction of Pluripotent Stem Cells from Mouse Embryonic and Adult Fibroblast Cultures by Defined Factors" *Cell*, Aug. 25, 2006, pp. 663-676, vol. 126.
Okita, K. et al. "Generation of germline-competent induced pluripotent stem cells" *Nature*, Jul. 19, 2007, pp. 313-318, vol. 448.
Yu, J. et al. "Induced Pluripotent Stem Cell Lines Derived from Human Somatic Cells" *Science*, Dec. 21, 2007, pp. 1917-1920, vol. 318.
Takahashi, K. et al. "Induction of Pluripotent Stem Cells from Adult Human Fibroblasts by Defined Factors" *Cell*, Nov. 30, 2007, pp. 861-872, vol. 131.
Hanna, J. et al. "Treatment of Sickle Cell Anemia Mouse Model with iPS Cells Generated from Autologous Skin" *Science*, Dec. 21, 2007, pp. 1920-1923, vol. 318.
Nakagawa, M. et al. "Generation of induced pluripotent stem cells without Myc from mouse and human fibroblasts" *Nature Biotechnology*, Jan. 2008, pp. 101-106, vol. 26, No. 1.
Stadtfeld, M. et al. "Induced Pluripotent Stem Cells Generated Without Viral Integration" *Science*, Nov. 7, 2008, pp. 945-949, vol. 322.
Okita, K. et al. "Generation of Mouse Induced Pluripotent Stem Cells Without Viral Vectors" *Science*, Nov. 7, 2008, pp. 949-953, vol. 322.
Chauhan, A. et al, "The taming of the cell penetrating domain of the HIV Tat: Myths and realities" *Journal of Controlled Release*, 2007, pp. 148-162, vol. 177.
Keller, G. "Embryonic stem cell differentiation: emergence of a new era in biology and medicine" *Genes & Development*, 2005, pp. 1129-1155, vol. 19.
Ying, Q.-L. et al, "Conversion of embryonic stem cells into neuroectodermal precursors in adherent monoculture" *Nature Biotechnology*, Feb. 2003, pp. 183-186, vol. 21.
Taranger, C. K. et al. "Induction of Dedifferentiation, Genomewide Transcriptional Programming, and Epigenetic Reprogramming by Extracts of Carcinoma and Embryonic Stem Cells" *Molecular Biology of the Cell*, Dec. 2005, pp. 5719-5735, vol. 16.
Chang, L. J. et al. "Self-Inactivating Lentiviral Vectors and a Sensitive Cre-loxP Reporter System" *Methods in Molecular Medicine*, 2003, pp. 367-382, vol. 76.
Frank, D. W. "The exoenzyme S regulon of Pseudomonas aeruginosa" *Molecular Microbiology*, 1997, pp. 621-629, vol. 26, No. 4.
Frithz-Lindsten, E. et al. "Intracellular targeting of exoenzyme S of *Pseudomonas aeruginosa* via type III-dependent translocation induces phagocytosis resistance, cytotoxicity and disruption of actin microfilaments" *Molecular Microbiology*, 1997, pp. 1125-1139, vol. 25, No. 6.
Shafikhani, S. H. et al. "Pseudomonas aeruginosa type III-secreted toxin ExoT inhibits host-cell division by targeting cytokinesis at multiple steps" *PNAS*, Oct. 17, 2006, pp. 15605-15610, vol. 103, No. 42.
Yahr, T. L. et al. "ExoY, an adenylate cyclase secreted by the *Pseudomonas aeruginosa* type III system" *Proceedings of the National Academy of Sciences USA*, Nov. 1998, pp. 13899-13904, vol. 95.
Kim, J. B. et al. "Oct4-Induced Pluripotency in Adult Neural Stem Cells" *Cells*, Feb. 6, 2009, pp. 411-419, vol. 136.
Kim, J. B. et al. "Direct reprogramming of human neural stem cells by OCT4" *Nature*, Oct. 1, 2009, pp. 649-654, vol. 461.

(Continued)

*Primary Examiner* — Thaian N Ton
(74) *Attorney, Agent, or Firm* — Saliwanchik, Lloyd & Eisenschenk

(57) ABSTRACT

A modified *P. aeruginosa* type III secretion system has been developed that efficiently delivers selected proteins into a host cell. In one example, a functional nuclear Cre Recombinase is injected into embryonic stem (ES) cells and can be used to induce pluripotent stem (iPS) cells. This method of in vitro lineage directed differentiation prevents insertional mutagenesis and provides a route to selected stem cell renewal and cell-based therapies.

15 Claims, 19 Drawing Sheets

(56) References Cited

PUBLICATIONS

Kim, J. B. et al. "Pluripotent stem cells induced from adult neural stem cells by reprogramming with two factors" *Nature*, Jul. 31, 2008, pp. 646-651, vol. 454.

Huangfu, D. et al. "Induction of pluripotent stem cells from primary human fibroblasts with only *Oct4* and *Sox2*" *Nature Biotechnology*, Nov. 2008, pp. 1269-1275, vol. 26, No. 11.

Hauser, A. R. "The type III secretion system of Pseudomonas aeruginosa: infection by injection" *Nature*, Sep. 2009, pp. 654-665, vol. 7.

Cornelis, G. R. "The type III secretion injectisome" *Nature Reviews*, Nov. 2006, pp. 811-825, vol. 4.

Lange, A. et al. "Classical Nuclear Localization Signals: Definition, Function, and Interaction with Importin α" *The Journal of Biological Chemistry*, Feb. 23, 2007, pp. 5101-5105, vol. 282, No. 8.

Palmer, E. et al. "Investigation into the use of C- and N-Terminal GFP fusion proteins for subcellular localization studies using reverse transfection microarrays" *Comp Funct Genom*, 2004, pp. 342-353, vol. 5.

\* cited by examiner

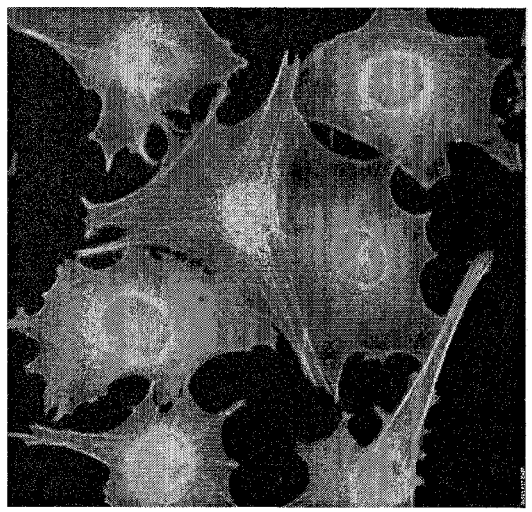
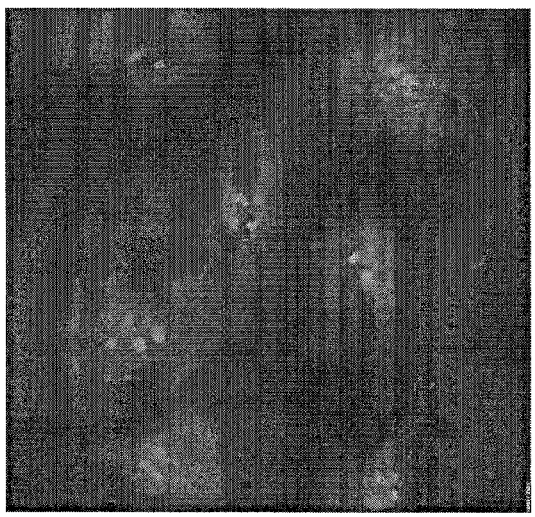
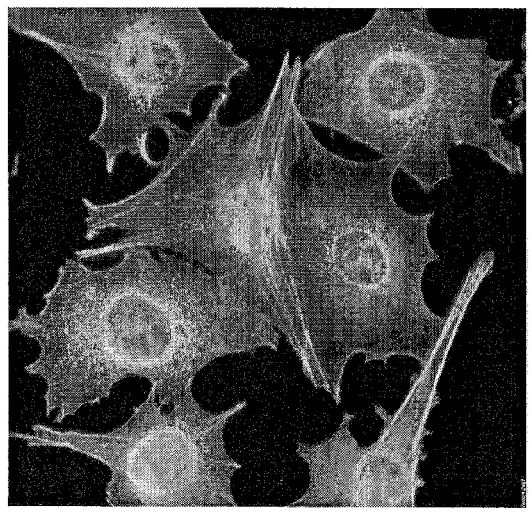
FIG. 3

FIG. 4A
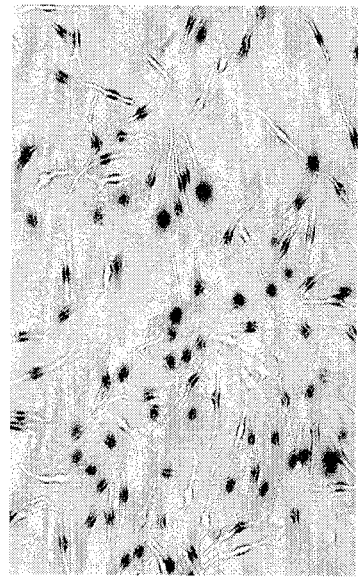
FIG. 4B
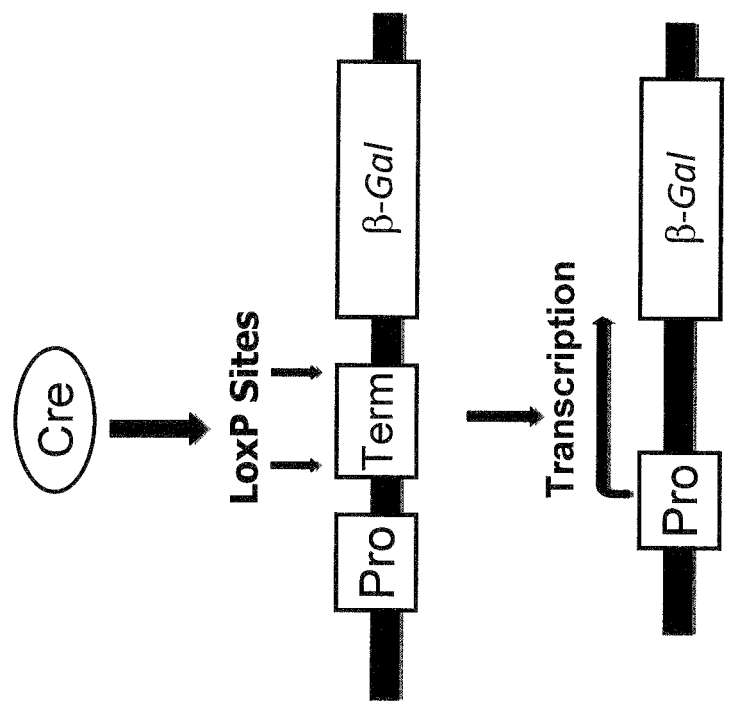

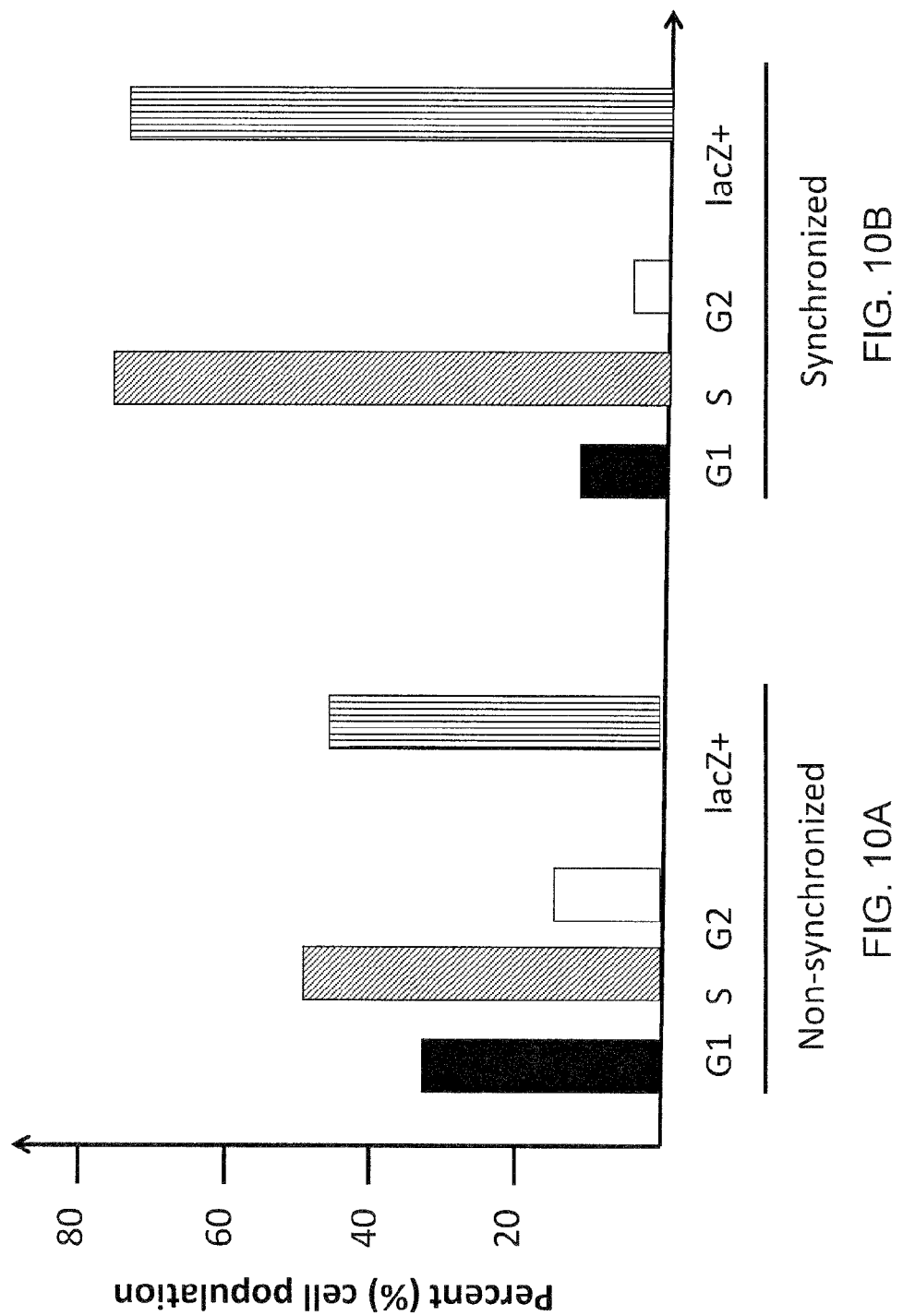

SEQUENCE LISTING

```
<160> NUMBER OF SEQ ID NOS: 21

<210> SEQ ID NO 1
<211> LENGTH: 35
<212> TYPE: DNA
<213> ORGANISM: Artificial Sequence
<220> FEATURE:
<223> OTHER INFORMATION: ExoS upstream primer

<400> SEQUENCE: 1
caaggaattc ggattatgcg gaggggttgc cggtg                              35

<210> SEQ ID NO 2
<211> LENGTH: 37
<212> TYPE: DNA
<213> ORGANISM: Artificial Sequence
<220> FEATURE:
<223> OTHER INFORMATION: ExoS upstream primer

<400> SEQUENCE: 2
gttgagatct cctgatgttt ctccgccagt ctaggaa                            37

<210> SEQ ID NO 3
<211> LENGTH: 36
<212> TYPE: DNA
```

```
<213> ORGANISM: Artificial Sequence
<220> FEATURE:
<223> OTHER INFORMATION: ExoS downstream primer

<400> SEQUENCE: 3
gtccagatct tggctcggca gcggatccgg gtggag                                  36

<210> SEQ ID NO 4
<211> LENGTH: 36
<212> TYPE: DNA
<213> ORGANISM: Artificial Sequence
<220> FEATURE:
<223> OTHER INFORMATION: ExoS downstream primer

<400> SEQUENCE: 4
tggaaagctt cgtcatcctc aatccgtacg gcaggc                                  36

<210> SEQ ID NO 5
<211> LENGTH: 37
<212> TYPE: DNA
<213> ORGANISM: Artificial Sequence
<220> FEATURE:
<223> OTHER INFORMATION: ExoT upstream primer

<400> SEQUENCE: 5
ggaggaattc gaaggggttg cgcaggcctg gctcgtc                                 37

<210> SEQ ID NO 6
<211> LENGTH: 37
<212> TYPE: DNA
<213> ORGANISM: Artificial Sequence
<220> FEATURE:
<223> OTHER INFORMATION: ExoT upstream primer

<400> SEQUENCE: 6
tgacggatcc tgatgtttcc ccgccagtct aggaacg                                 37

<210> SEQ ID NO 7
<211> LENGTH: 37
<212> TYPE: DNA
<213> ORGANISM: Artificial Sequence
<220> FEATURE:
<223> OTHER INFORMATION: ExoT downstream primer

<400> SEQUENCE: 7
cggaggatcc caaggggtgt ccgttttcat ttgcgcc                                 37

<210> SEQ ID NO 8
<211> LENGTH: 36
<212> TYPE: DNA
<213> ORGANISM: Artificial Sequence
<220> FEATURE:
<223> OTHER INFORMATION: ExoT downstream primer

<400> SEQUENCE: 8
aggtaagctt ccagcgcctg cgcctgggcc tccttg                                  36

<210> SEQ ID NO 9
<211> LENGTH: 39
<212> TYPE: DNA
<213> ORGANISM: Artificial Sequence
<220> FEATURE:
<223> OTHER INFORMATION: ExoY upstream primer

<400> SEQUENCE: 9
aactgaattc cgaggatgtc gccctgctcg accatcggg                               39
```

```
<210> SEQ ID NO 10
<211> LENGTH: 37
<212> TYPE: DNA
<213> ORGANISM: Artificial Sequence
<220> FEATURE:
<223> OTHER INFORMATION: ExoY upstream primer

<400> SEQUENCE: 10
cccaggatcc aggaggcgct cgactttttc caacgta                                37

<210> SEQ ID NO 11
<211> LENGTH: 36
<212> TYPE: DNA
<213> ORGANISM: Artificial Sequence
<220> FEATURE:
<223> OTHER INFORMATION: ExoY downstream primer

<400> SEQUENCE: 11
ataaggatcc gggcagcggc gagatatcag aaaacg                                 36

<210> SEQ ID NO 12
<211> LENGTH: 37
<212> TYPE: DNA
<213> ORGANISM: Artificial Sequence
<220> FEATURE:
<223> OTHER INFORMATION: ExoY downstream primer

<400> SEQUENCE: 12
cgttaagctt gagatagccg agcatgctca ggccgtc                                37

<210> SEQ ID NO 13
<211> LENGTH: 33
<212> TYPE: DNA
<213> ORGANISM: Artificial Sequence
<220> FEATURE:
<223> OTHER INFORMATION: ExoS-upstream

<400> SEQUENCE: 13
gacgaattcg gcgtcttccg agtcactgga ggc                                    33

<210> SEQ ID NO 14
<211> LENGTH: 32
<212> TYPE: DNA
<213> ORGANISM: Artificial Sequence
<220> FEATURE:
<223> OTHER INFORMATION: ExoS17 downstream

<400> SEQUENCE: 14
gacgagtcgt gcaattcgac ggcgaaagac gg                                     32

<210> SEQ ID NO 15
<211> LENGTH: 34
<212> TYPE: DNA
<213> ORGANISM: Artificial Sequence
<220> FEATURE:
<223> OTHER INFORMATION: ExoS54 downstream

<400> SEQUENCE: 15
gagctcgagc agcccctcac ccttcggcgc gtcc                                   34

<210> SEQ ID NO 16
<211> LENGTH: 33
<212> TYPE: DNA
<213> ORGANISM: Artificial Sequence
<220> FEATURE:
<223> OTHER INFORMATION: ExoS96 downstream
```

```
<400> SEQUENCE: 16
gacgagctcg gacatcagcg caggctgcgc gtc                          33

<210> SEQ ID NO 17
<211> LENGTH: 33
<212> TYPE: DNA
<213> ORGANISM: Artificial Sequence
<220> FEATURE:
<223> OTHER INFORMATION: ExoS129 downstream

<400> SEQUENCE: 17
gacgagctct tccggtgtca gggtcgccag ctc                          33

<210> SEQ ID NO 18
<211> LENGTH: 33
<212> TYPE: DNA
<213> ORGANISM: Artificial Sequence
<220> FEATURE:
<223> OTHER INFORMATION: ExoS234 downstream

<400> SEQUENCE: 18
gacgagctcc ttgtcggccg atactctgct gac                          33

<210> SEQ ID NO 19
<211> LENGTH: 33
<212> TYPE: DNA
<213> ORGANISM: Artificial Sequence
<220> FEATURE:
<223> OTHER INFORMATION: ExoS full downstream

<400> SEQUENCE: 19
gacgagctcg gccagatcaa ggccgcgcat cct                          33

<210> SEQ ID NO 20
<211> LENGTH: 31
<212> TYPE: DNA
<213> ORGANISM: Artificial Sequence
<220> FEATURE:
<223> OTHER INFORMATION: Cre upstream

<400> SEQUENCE: 20
ggagctcatg cctaagaaga acgaaagat c                             31

<210> SEQ ID NO 21
<211> LENGTH: 26
<212> TYPE: DNA
<213> ORGANISM: Artificial Sequence
<220> FEATURE:
<223> OTHER INFORMATION: Cre downstream

<400> SEQUENCE: 21
cgaggtcgac ggtatcgata agcttg                                  26
```

BACTERIAL MEDIATED DELIVERY OF NUCLEAR PROTEIN INTO PLURIPOTENT AND DIFFERENTIATED CELLS

This invention was made with government support under National Institutes of Health Grant No. GM 091238. The government has certain rights in the invention.

FIELD OF THE INVENTION

The invention concerns genetic engineering of bacteria for delivery of differentiation factors into eukaryotic cells.

DESCRIPTION OF BACKGROUND ART

Stem cells have been the subject of intensive research due to potential for therapeutic applications such as tissue and organ regeneration. Pluripotent stem cells are capable of self renewal and differentiation into a diverse array of specialized cells. These can be further divided, by their derivation into adult and embryonic stem (ES) cells. ES cells are immortal cells obtained from the blastocyst inner call mass, which are able to differential into any cell of the three primary germ layers (pluripotent).

Adult stem cell populations can be found in the germline and somatic tissues, but are comparatively limited in abundance, self renewability and potency. While stem cells are a powerful tool in the examination of developmental and disease pathways, the great hope for ES cells has been invested primarily in regenerative therapy for genetic metabolic and degenerative disorders.

Somatic cell nuclear transfer (SCNT) has been used to insert the nuclei of specific somatic cells into enucleated oocytes to obtain ES cells that are nearly identical to the donor. While nuclear reprogramming has been achieved by fusion of ES with somatic cells (Yu, et al., 2006), the inefficiency of the fusion process is a major limiting factor. The major drawbacks of these methods are largely due to the embryonic derivation of the stem cells and the incidence of immune rejection.

To circumvent these issues, several groups have begun examining the trans-acting factors that enable reprogramming of somatic cell nuclei to a pluripotent state after SCNT or ES cell fusion. Taranger, et al., (2005) have been able to induce pluripotency in epithelial 293T cells by incubation with embryonic stem cell extracts. Takahashi and Yamanaka (2006) demonstrated that retroviral mediated transduction of four transcriptional factors, which are upregulated in ES cells, can reprogram murine adult and embryonic fibroblasts to a pluripotent state. The group screened several potential factors, finding that Oct3/4, Sox2, c-Myc and Klf4 were sufficient to induce pluripotent stem cells (iPS). The iPS cells showed gene expression and morphology similar to mES cells. Pluripotency of the fibroblast derived iPS cells was demonstrated by their ability to transmit through germ line (Okita, 2007).

Takahashi (2007) reprogrammed human dermal fibroblasts (HDF) to iPS using the same four factors. These HDF derived iPS also showed morphology, gene expression and teratoma formation similar to ES cells, as well as reduced methylation of oct4, rex1 and nanog promoters compared to the parental HDF cells. iPS-HDF were also able to undergo directed differentiation into neuronal cells, and even cardiomyocytes that began beating 12 days after induction of differentiation. Simultaneously, another group in Wisconsin reported that similar set of genes (oct4, sox2, lin28 and nanog) were sufficient to reprogram fetal lung fibroblasts and neonatal foreskin fibroblasts into iPS cells (Yu, 2007).

Unlike SCNT or ES-Somatic cell fusion methods of nuclear reprogramming, induction of pluripotency by introduction of defined transcription factors generates completely individual-specific stem cells, eliminating alteration of cell ploidy and the need for oocytes or previously existing stem cells. iPS cells can generate not only individual specific but also disease specific stem cells, allowing for enhanced testing of therapeutic drug efficacy.

Several laboratories have repeated these experiments, generating iPS from fibroblasts from mouse hepatocytes and gastric epithelial cell, and have demonstrated pluripotency by directed differentiation to several cell types, including neuronal, cardiovascular and hematopoietic lineages. Using a mouse model for sickle cell anemia, Hanna et al., (2007) generated iPS cells from autologous mouse skin cells, and repaired genetic mutations via homologous recombination. The repaired iPS cells were then directed to differentiation into hematopoietic progenitors, transplanted into the irradiated sickle cell anemia model mice and able to treat the disorder, illustrating the therapeutic potential of iPS cells.

While induction of pluripotency in somatic cells is at least a step forward in developing iPS cell for clinical application, significant concerns with the reported methods arise from the use of a retroviral vector. The integration site or number of copies of each gene transduced cannot be controlled. Uncontrolled genomic integration potentially interrupts critical genes, such as tumor suppressors, or alters transcriptional regulation of other genes, including oncogenes. Additionally, the use of c-myc, a known oncogene may contribute to the finding that 20% of the mice derived from iPS cells developed tumors (Okita, 2007). iPS cells have been successfully generated without the use of c-myc; however, the efficiency is significantly reduced (Nakagawa, 2008).

Okita (2008) and Stadtfeld (2008) utilized either adenoviral vector-mediated gene transfer or direct plasmid DNA transfection to generate iPS cells without an apparent trace of gene integration. However, as long as DNA molecules are introduced, the potential of DNA integration can not be totally eliminated. There remains a need for alternative methods for a safe clinical application of the iPS cells.

ES cells are pluripotent cells derived from the inner cell mass of the pre-implantation blastocyst. The distinguishing characteristics of ES cells, not possessed by other organ-specific stem cells, are the capacity to undergo robust self-renewal in cell culture while retaining a pluripotency for differentiation. These characteristics of ES cells have attracted attention for their use in cell-based transplantation therapy or tissue engineering; particularly after human ES cells were isolated in 1998.

To facilitate the use of pluripotent ES cells in cell transplantation, there are two major hurdles that need to be overcome. First, immune rejection by the recipients. Recently Induced pluripotent stem (iPS) cells, as discussed above, have yet to be developed as individual specific iPS cells. While establishing a human ES cell bank is also a valid alternative, a more difficult obstacle is the heterogenic nature of the cell population obtained from ES cell differentiation, primarily due to low efficiency of differentiation.

For most cell lineages, despite intensive studies in the field, it remains a difficult task to generate specific cell types from ES cells with high purity and efficiency. Before one can promote the development of cell types of interest from ES cells for clinical applications, there needs to be a consistent and reproducible record of successful lineage direction in vitro.

Three general approaches have been used to initiate ES cell differentiations. In the most popular method, ES cells are allowed to aggregate to form three-dimensional colonies known as embryoid bodies (EBs). Alternatively, ES cells are cultured directly on stromal cells and differentiation takes place upon contact with these cells. A third protocol involves differentiating ES cells in a monolayer on extracellular matrix proteins. Each of these three approaches has specific advantages and disadvantages, as reviewed by Keller et al. (2005).

Combining these three basic protocols, several differentiating protocols have been developed by varying serum concentration or by the use of a complex cocktail of growth factors and cytokines, extra cellular matrix proteins and small chemicals. Although these approaches have met with some success in neuroectodermal or neural specification (Ying, 2003, for example), it has proved difficult to enrich most of the other cell types, such as cardiomyocytes and hepatocytes, without the use of drug-resistant genes or fluorescent markers.

To differentiate ES cells for cell-based therapies, permanent genetic modification poses the danger of oncogenic transformation or other unforeseen changes upon implantation of the cells into an individual. The use of growth factors, cytokines and chemicals to drive ES cell differentiation into cardiomyocytes has had limited success, therefore a system was developed to directly introduce the regulatory proteins into ES cells to trigger the differentiation. Transfection reagent is toxic to the ES cells and the efficiency of transfection is low. And although protein factors can also be translocated into the host cells through a protein translocation domain (PTD), their translocation efficiency is generally low and limited to small sized proteins (Chauhan, 2007). This is further complicated by the fact that obtaining sufficient soluble protein is a challenge because most proteins tend to form inclusion bodies upon over expression.

SUMMARY OF THE INVENTION

The invention is a method for reprogramming a host cell by taking advantage of a bacterial mechanism for introducing proteins into a host cell. A pseudomonad species of bacteria has been modified to reduce host cell toxicity while retaining the efficiency of its delivery system. In particular, a mutant gram negative bacterium has been created which can be used as a tool to introduce selected proteins into a wide range of cells, including ES as well as adult cells.

Accordingly, highly effective system for delivering proteins into eukaryotic cells has been developed. A bacterial strain, illustrated with *P. aeruginosa*, was engineered to eliminate toxicity toward the host cell while maintaining the ability to efficiently introduce transformation factors into the cell. Using this delivery method, it is possible to directly introduce differentiation factors into a host cell from a needle-like structure on the bacterial surface.

This structure, identified as a type III secretion system (T3SS), is a naturally occurring protein delivery mechanism found in several Gram negative bacteria, including *Pseudomonas aeruginosa*. The injectisome component is illustrated in FIG. 1 showing the transmembrane protein complex forming the inner and outer membrane of the Gram negative plasma membrane. Protein translocation is effected directly from the bacterium into the host cell cytoplasm.

The T3SS surface structure encoded by many Gram-negative bacteria is designed to inject bacterial proteins directly into cytoplasmic compartment of the host cells. The needles are inserted into the host cell membrane and inject the protein effector molecules. Injection of bacterial effectors into host cells results in a various physiological changes, ranging from morphological alteration (facilitate or block invasion) to killing of the host cells (immune cells), all of which provide the bacterial pathogen with a survival advantage within the host environment The whole injection process takes place in a very short time.

Some type III secretion systems are activated by bacterial contact with host cell surfaces. Individual type III secretion systems direct the secretion and translocation of a variety of unrelated proteins, which account for species-specific pathogenesis phenotypes. In contrast to the secreted virulence factors, most of the 15 to 20 membrane-associated proteins which constitute the type III secretion apparatus are conserved among different pathogens. The genes encoding type III secretion systems are clustered, and various pieces of evidence suggest that these systems have been acquired by horizontal genetic transfer during evolution. Expression of type III secretion systems is coordinated and regulated in response to host environmental stimuli by networks of transcription factors. Animal pathogens having type III secretion systems include *Yersinia* spp., *Pseudomonas aeruginosa, Shigella flexneri, Salmonella typhimurium*, enteropathogenic *Escherichia coli*, and *Chlamydia* spp. (Hueck, 1998). A review of structure function regulation and impact on host cells is found in the Hueck reference.

There are at least 140 species of *Pseudomonas* including *Pseudomonas abietaniphila; P. agarici; P. agarolyticus; P. alcaliphila; P. alginovora; P. andersonii; P. antarctica; P. asplenii; P. azelaica; P. batumici; P. borealis; P. brassicacearum; P. chloritidismutans; P. cremoricolorata; P. diterpeniphila; P. filiscindens; P. frederiksbergensis; P. gingeri; P. graminis; P. grimontii; P. halodenitrificans; P. halophila; P. hibiscicola; P. hydrogenovora; P. indica; P. japonica; P. jessenii; P. kilonensis; P. koreensis; P. lini; P. lurida; P. lutea; P. marginata; P. meridiana; P. mesoacidophila; P. pachastrellae; P. palleroniana; P. parafulva; P. pavonanceae; P. proteolyica; P. psychrophila; P. psychrotolerans; P. pudica; P. rathonis; P. reactans; P. rhizosphaerae; P. salmononii; P. thermaerum; P. thermocarboxydovorans; P. thermotolerans; P. thivervalensis; P. umsongensis; P. vancouverensis; P. wisconsinensis; P. xanthomarina*; and *P. xiamenensis; P.* sp.

Group members among the species include:

*P. aeruginosa* group: *P. aeruginosa; P. akaligenes; P. anguilliseptica; P. citronellolis; P. flavescens; P. jinjuensis; P. mendocina; P. nitroreducens; P. oleovorans; P. pseudoalcaligenes; P. resinovorans; P. straminae;*

*P. chloroaphis* group: *P. aurantiaca; P. chlororaphis; P.s fragi; P. lundensis; P. taetrolens;*

*P. fluorescens* group: *P. azotoformans; P. brenneri; P. cedrina; P. congelans; P. corrugata; P. costantinii; P. extremorientalis; P. fluorescens; P. fulgida; P. gessardii; P. libanensis; P. mandelii; P. marginalis; P. mediterranea; P. migulae; P. mucidolens; P. orientalis; P. poae; P. rhodesiae; P. synxantha; P. tolaasii; P. trivialis; P. veronii;*

*P. pertucinogena* group: *P. denitrificans; P. pertucinogena P. putida* group: *P. fulva; P. monteilii; P. mosselii; P. oryzihabitans; P. plecoglossicida; P. putida;*

*P. stutzeri* group: *P. balearica; P. luteola, P. stutzeri;*

*P. syringae* group: *P. avellanae; P. cannabina; P. caricapapyae; P. cichorii; P. coronafaciens; P. fuscovaginae; P. tremae; P. viridiflava.*

The T3SS of the *P. aeruginosa* mutant described herein has effectively delivered transcriptional factors such as Oct4 or padx1 into eukaryotic cells and embryonic stem (ES) cells. Functionality was demonstrated by targeting a recombinase to the host cell nucleus to promote chromosome recombination in mammalian cells. The invention thus provides a route to reprogramming already differentiated eukaryotic cells to ES-like cell populations or from pluripotent stem cells (ES or iPSC) into lineage specific cell population.

*Pseudomonas aeruginosa* is a ubiquitous opportunistic pathogen, which secretes relatively few exotoxins by a single T3SS. Type III secretion is highly regulated in *P. aeruginosa*, and can be induced in vitro by low extracellular calcium levels and direct host cell contact. Once activated, *P. aeruginosa* secretes three of four exotoxins: ExoS and ExoT, which possess both ADP ribosyltransferase and GTPase activating protein activity; ExoY, an adenylyl cyclase; and ExoU, a lipase with hemolyic activity. Ultimately, injection of these toxins results in host cell rounding and death, rendering the bacterial survival advantage within the host environment. Of these effectors, the functional domains of ExoS are best characterized. Previous studies have shown that various lengths of the amino-terminus of ExoS can be fused to exogenous proteins and direct them for injection into the host cell cytosol in a type III secretion dependent manner. While one such study has demonstrated the functionality of these injected fusion proteins by ex vivo complementation of a cytoplasmic protein deficiency, the type III secretion system has not yet been applied to the delivery of nuclear proteins.

The development of a simple, efficient system for introduction of nuclear proteins would meet an emerging need which has been made quite apparent in recent studies. While the ability to reprogram terminally differentiated nuclei to a pluripotent state by forced expression of key transcription factors (Oct4, Sox2, cMyc, Klf4) has been demonstrated, the therapeutic application of these reprogrammed cells is severely hindered by the integration of oncogenic transgenes. There have been numerous attempts to overcome this limitation, including the use of DNA reprogramming cassettes which can be excised by Cre recombinase once cells have been stably reprogrammed. Cre is a site specific, bacteriophage derived recombinase which begets homologous recombination between sequences known as LoxP sites. A DNA sequence flanked by direct repeat of LoxP sites is excised upon Cre mediated recombination. This Cre-loxP system is widely used in modern molecular biology and is particularly useful in the generation of conditional gene knockouts.

The *P. aeruginosa* type III secretion system has been used as an alternative method to deliver functional Cre recombinase to the nuclei of differentiated and pluripotent cells in vitro as well as Cre mice in vivo. DNA recombination through loxP sites on the chromosome has been achieved, resulting in alteration of host cell gene expression. Neither the transient bacterial infection nor the bacterially delivered Cre affected the pluripotency of the mouse ES cell or iPS cells. This work paves the way for future application of a novel protein delivery technology in therapeutic cellular reprogramming, as this is a safe alternative to the current gene delivery mediated reprogramming method.

BRIEF DESCRIPTION OF THE FIGURES

FIG. 3 shows immunostaining of ExoS-Flag injected into MEF cells. Cells were stained with anti-Flag as primary antibody and secondary Ab that was labeled with FITC. Nuclei were stained with PI.

FIG. 4 shows the reporter system for the translocation of Cre recombinase. The reporter cell line TE26 was stained for β-galactosidase following infection by *P. aeruginosa* that do not code for Cre (A) or encodes ExoS54-Cre fusion (B).

FIG. 10A. Effect of Cell Cycle on Cre Recombination is shown in FIGS. 10A-B. Te26 cells were synchronized by double thymidine treatment and cell cycle state was assessed by FACS analysis. Distribution of cell population at indicated time after thymidine release.

FIG. 10B. LacZ positive Te26 cells after infection of the corresponding cell population at MOI 50 for 3 hours.

DETAILED DESCRIPTION OF THE INVENTION

Figure 1:
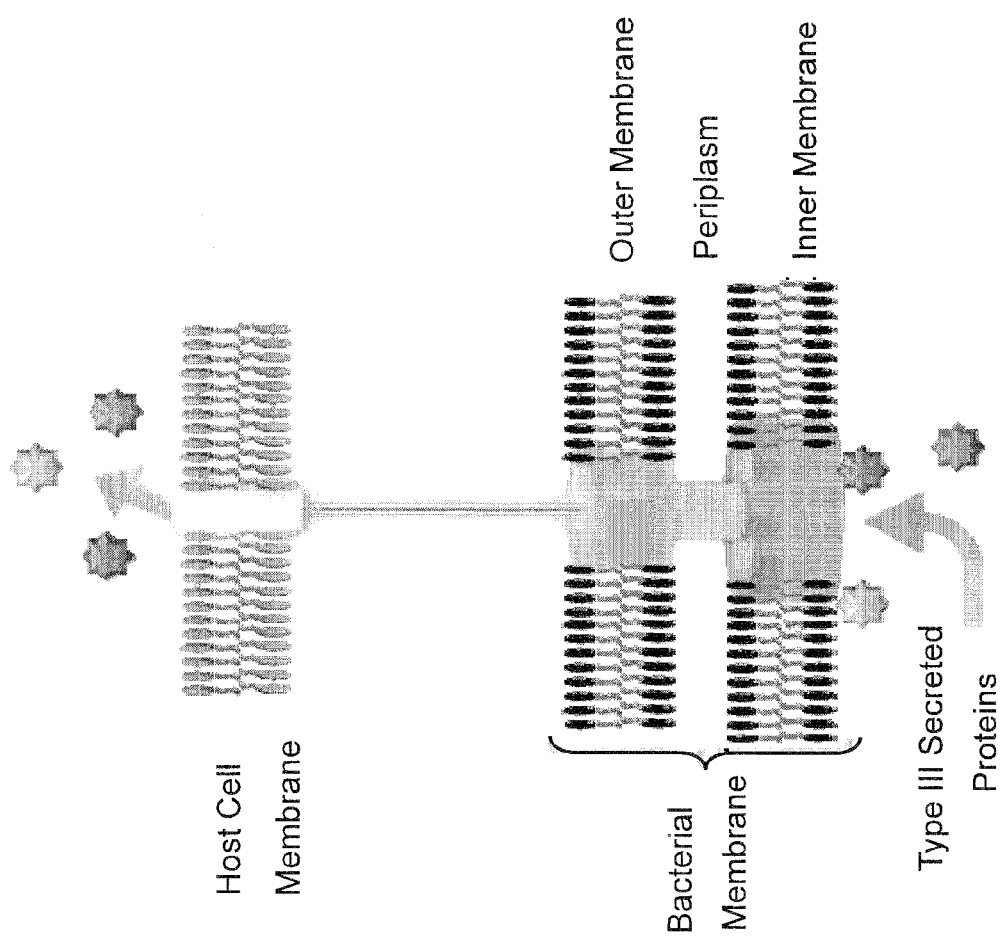
FIG. 1 illustrates the Type III bacterial secretion system. The injectisome is a transmembrane protein complex, which generates a needle-like projection from the bacterial outer membrane, capable of protein translocation from the bacterium directly into the host cell cytoplasm.

The invention described herein demonstrates that modification of a T3SS bacterial delivery system by eliminating toxicity toward the host cell confers a number of advantages in utilizing a naturally occurring protein delivery system to deliver and induce ES cell differentiation.

First, rather than genetic material (DNA or RNA), target proteins are directly delivered into the ES cells, thus causing no genetic alteration in the recipient cells.

Second, the injection system is highly efficient, delivering effector proteins easily to 100% of the target cells in a very short period of time.

Third, the delivery system is easy to manipulate because there is a firm understanding of its structure, function and regulation.

Finally, the non-toxic bacterial cells can easily be removed from host cells by antibiotic treatment following the protein delivery.

One objective of this work was to use a *P. aeruginosa* encoded T3SS to deliver key protein factors regulating ES cell differentiation in order to demonstrate that direct protein delivery can be an effective alternative to the permanent genetic modification for ES cell differentiation.

In the iPS cell lines reported by Okita as discussed in the Background, the transgenes introduced by the retrovirus appear to be silenced in the reprogramming process while the endogenous genes were reactivated. If reprogramming into iPS requires only transient signaling to turn on the endogenous gene activation, alternative approaches to trigger iPS production other than use of retroviruses which can introduce potentially harmful genes into the host cell were considered. Although a number of reports demonstrated that certain small molecular weight chemicals facilitate or replace one or two reprogramming factors, it was considered unlikely that reprogramming could be achieved using small molecules alone.

A more realistic approach was thought to be to directly introduce regulatory proteins into the cells to trigger the reprogramming. Transfection reagent mediated introduction of proteins was considered a possibility; however, the transfection process was known to be quite toxic to the cells; moreover, the efficiency of transfection is generally low and varies greatly depending on cell lines used.

Protein factors can be introduced into the host cells through a protein translocation domain (PTD). Unfortunately, as is known in the art, translocation efficiency is generally low and limited to small sized proteins; additionally, obtaining sufficient soluble protein is a challenge because these proteins tend to form inclusion bodies upon overexpression.

While the ability of *P. aeruginosa* to infect an assortment of cell types in vitro has been well established, there did not appear to be any indication that it had or would be expected to have capacity to infect pluripotent cells. Taking into consideration the need for translocation and the goal of cell reprogramming, a method based on use of the naturally occurring protein T3SS delivery machinery in a modified *P. aeruginosa* was investigated.

*P. aeruginosa* is a ubiquitous, opportunistic pathogen, the virulence of which is dependent upon delivery of toxic proteins into host cells through T3SS. The T3SS is designed to inject bacterial protein toxins directly into cytoplasmic compartment of the host cells (FIG. 1). The needles are inserted into the host cell membrane and inject the protein effector molecules. Injection of the bacterial effectors into the host cells results in various physiological changes, ranging from morphological alteration (facilitate invasion or block phagocytosis) to killing of the host cells (immune cells), all of which render the bacterial pathogen a survival advantage within the host environment.

T3SS is highly efficient in injecting effector proteins into host cells and the whole process takes place in a short period of time. The mechanism of such injection has been well studied. The efficiency of injection by wild type *P. aeruginosa* can easily reach 100% with MOI>20 in a short injection time. Since this naturally occurring protein injection machinery does not involve DNA integration, we believe at least in principle at one time thought to be ideal for the delivery of the key regulatory proteins to drive cell differentiation.

Among the attractive features of using *P. aeruginosa* is the ease of eliminating the bacterial cells without harming the host cells by the addition of antibiotics or use of conditional lethal mutants. Because of such ease of manipulation, the T3SS was considered for development in various protein delivery applications.

Unfortunately, despite others' studies of the T3SS system and limited success in protein delivery, cytotoxicity toward the host cell has remained a major concern. With this in mind, but recognizing and wishing to take advantage of the potential efficiency of the T3SS system, a non-cytotoxic strain was developed by deleting all major virulence factors. The aim was to reduce toxicity toward the host cell without loss of the injection efficiency. Indeed, successful and efficient delivery of recombinant nuclear proteins with significantly reduced toxicity to the host was demonstrated with both a human carcinoma cell line as well as mouse ES cells. The following indicates several of the steps and rationale utilized in developing the bacterial mediated delivery of proteins into both pluripotent and differentiated cells.

Characterization of a Hyper Type III Secreting Strain of *P. Aeruginosa*.

Figure 6:
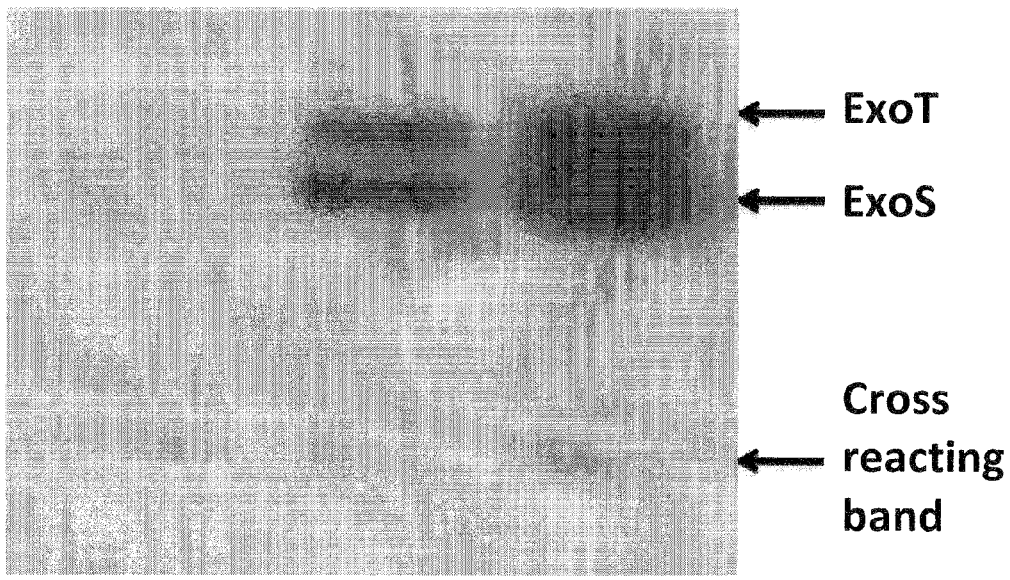
FIG. 6 shows comparison of ExoS secretion by standard laboratory strains of PAO1, PAK and a hyper secretion strain K-J. Strains were grown in L-broth plus 5 mM EGTA for 3 hr and 10 ul culture supernatants were subjected to Western blot using anti-ExoS antibody which recognizes both ExoS and ExoT.

The standard laboratory strain of *P. aeruginosa* (PAO1), whose genome has been sequenced, secretes low levels of type III effectors under type III inducing conditions. To identify a strain with elevated type III secretion, a number of *P. aeruginosa* strains were screened, including commonly used laboratory strains as well as clinical and environmental isolates. A laboratory strain of PAK that had been passaged for over 10 years displayed the highest level of ExoS secretion under type III inducing conditions (hereafter referred to PAK-J) (FIG. 6). According to quantitative ELISA assays, this strain secretes 10 mg/ml ExoS into the culture supernatant, which is more than 10 times higher than those secreted by most other strains. Infection of cultured mammalian cells by this strain caused significantly higher cytotoxicity, resulting in complete rounding and lifting of various adhering cells, such as HeLa and mouse embryonic fibroblast (MEF), within 3 hours at an MOI of 20.

Generation of a *P. Aeruginosa* Strain with Reduced Cytotoxicity.

Figure 7:
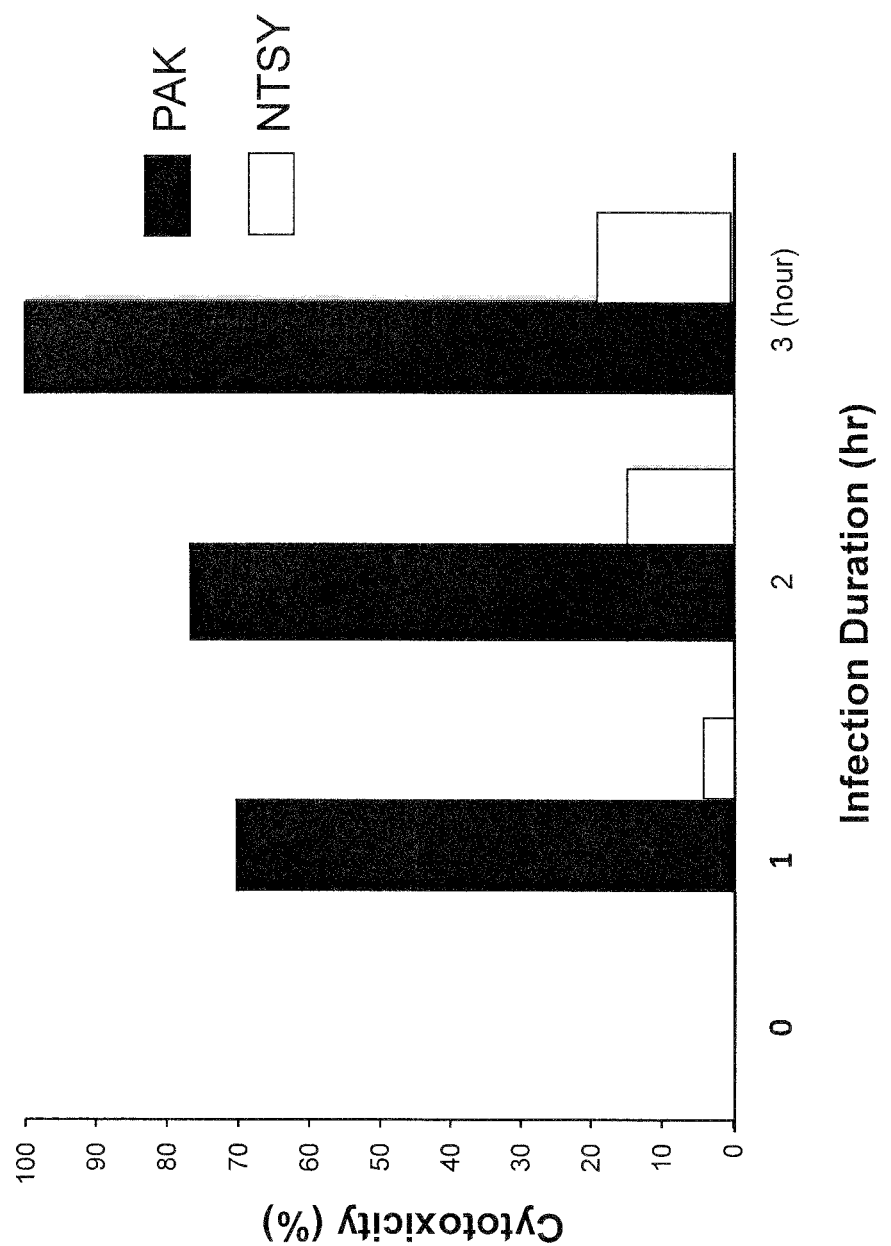
FIG. 7 shows reduction of exotoxin mediated cytotoxicity. Te26 cells were infected with PAKΔJ or PAK-J STY at a MOI of 100 for the indicated time. 24 hr post infection, culture media were subjected to LDH release assay to determine relative cell death.

The *P. aeruginosa* strain PAK-J expresses three type III secreted effectors, ExoS, ExoT and ExoY, potent exotoxins that account for much of the cytotoxicity associated with this bacterium. In order to maximize protein injection, the delivery strain must be capable of prolonged incubation with host cells. As such, it was necessary to delete these genes from the PAK-J chromosome by successive unmarked allelic exchange. The resulting strain, PAK-JΔSTY, has comparatively reduced cytotoxicity, which is obvious by visual observation after infection of HeLa cells. In order to quantify this diminished toxicity, lactate dehydrogenase (LDH) and Crystal Violet assays were performed. LDH is a stable cytosolic enzyme that is released into the culture media upon cell death and a colorimetric assay can be used to quantify the relative levels of LDH. After infections of various durations, samples were collected from the cell culture media and analyzed for LDH content. LDH release after infection with PAK-JΔSTY was significantly lower than the wild-type PAK-J, and increased in a dose and time dependent manner (FIG. 7). After obtaining LDH samples, the wells of the 12-well plate were stained with Crystal violet to determine the relative proportion of viable adhering cells after infection with each strain. The Crystal violet assay further validated the findings of the LDH release assay (data not shown). Combined, these results indicates that deletion of the PAK-J type III secreted exotoxins reduces in vitro cytotoxicity by approximately 80%. This diminution in cytotoxicity resulted in increased infection duration, and thus enhanced protein delivery by the type III secretion.

Secretion of Cre Recombinase Through the Bacterial T3SS.

The bacteriophage derived Cre recombinase is a widely used genetic tool which allows for excision of DNA between two LoxP sequences by homologous recombination. The Cre-Lox system was chosen to demonstrate the utility of this bacterial protein delivery system primarily because it is a DNA-interacting protein which must localize to the nucleus to exert its recombinase activity. Additionally, there are many Cre-dependent reporter cell lines readily available, making this a very convenient assay system.

Figure 8A:
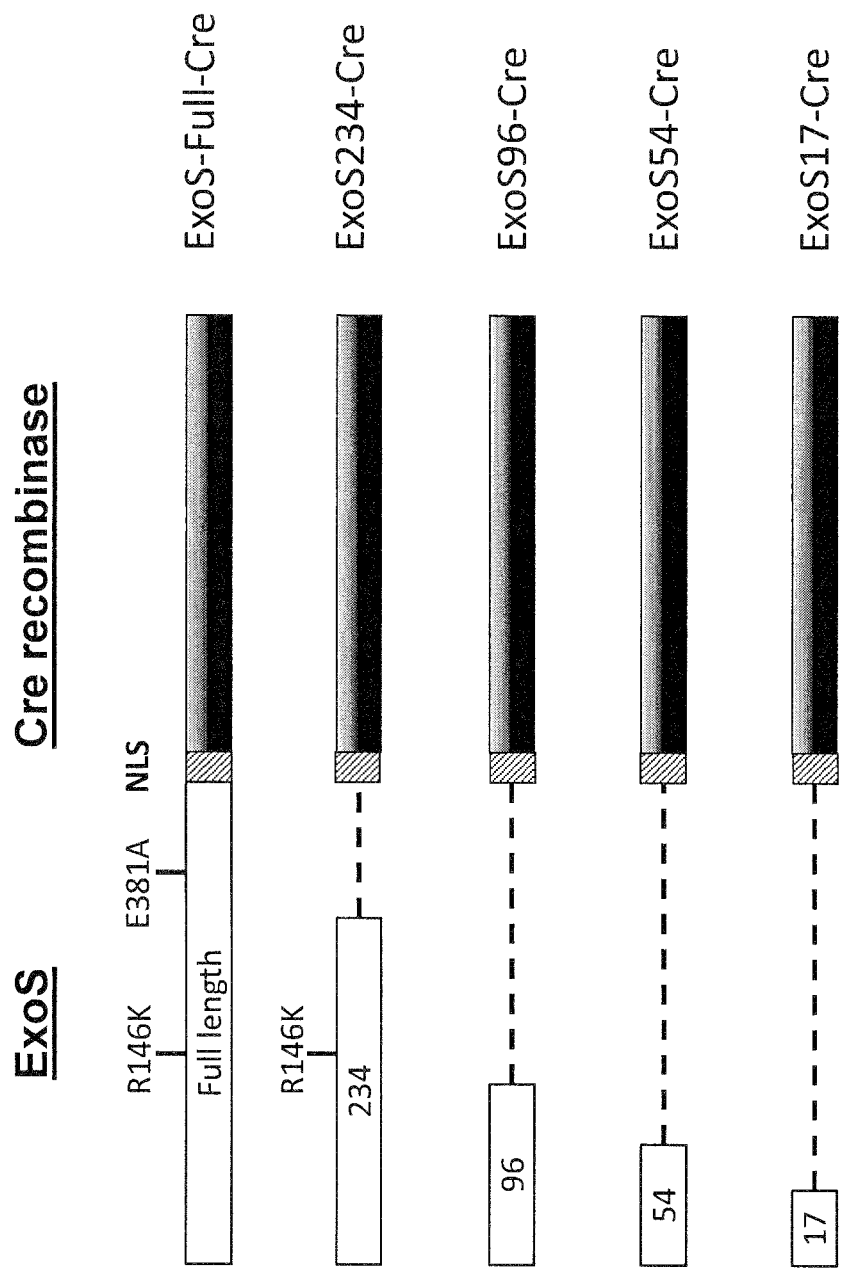
FIG. 8A. Cre recombinase was fused in frame with various N-terminal portions of ExoS, with a nuclear localization sequence (NLS) in the fusion junction.
Figure 8B:
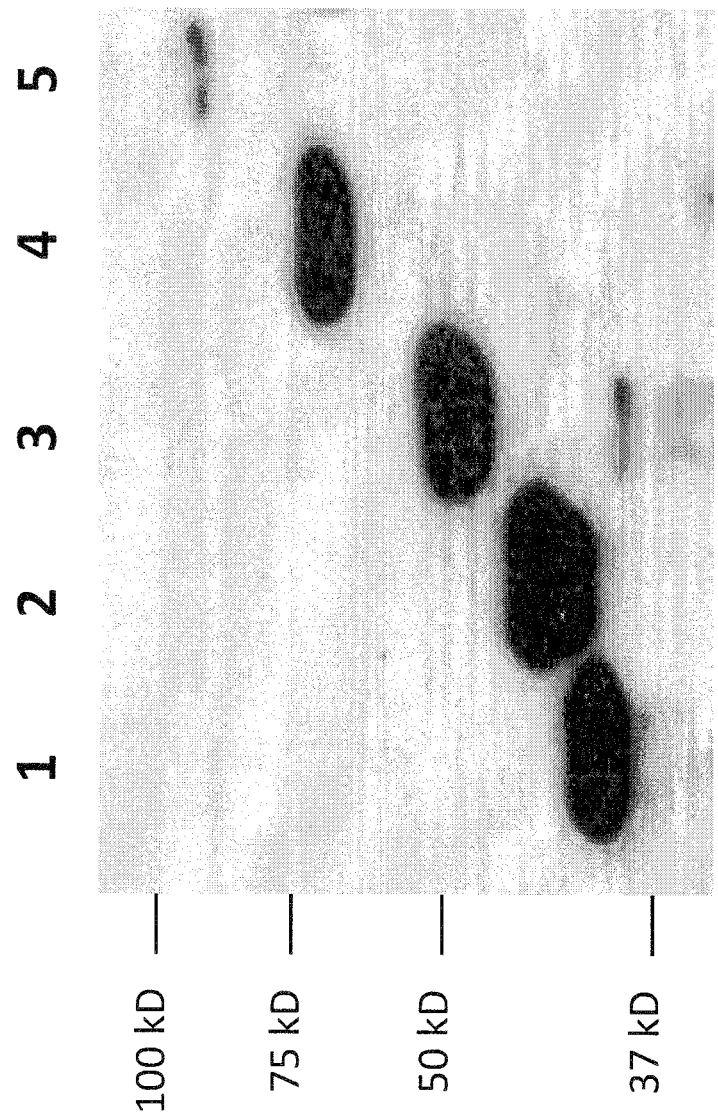
FIG. 8B. PAK-JΔSTY containing each construct was subjected to type III induction and cell pellet was assayed for fusion protein production by Western blot against Cre. Lane 1-5 are Cre fusions to ExoS17, ExoS54, ExoS96, ExoS234 and ExoS full length, respectively.

Previous studies had demonstrated various lengths of the amino-terminus of ExoS to be capable of directing exogenous proteins to the injectisome for type III secretion, however the efficiency of each signal sequence varies by protein. In order to determine the optimal signal sequence for delivery of the Cre, fusions of various lengths of ExoS to Cre recombinase were generated, with the addition of a nuclear localization sequence in the fusion junction (FIG. 8A). Each construct was then introduced into PAK-JΔSTY by electroporation and tested for proper expression under type III inducing condition as well as efficiency of T3SS mediated injection into host cells. PAK-JΔSTY strains containing the various fusion constructs were grown in L-broth plus 5 mM EGTA for 3 hours to induce type III secretion system genes. Cell pellets were separated on SDS-PAGE and subjected to Western Blotting with an antibody against Cre recombinase. As indicated in FIG. 8B, all fusion proteins were made equally, except for the full length ExoS fusion.

Figure 8C:
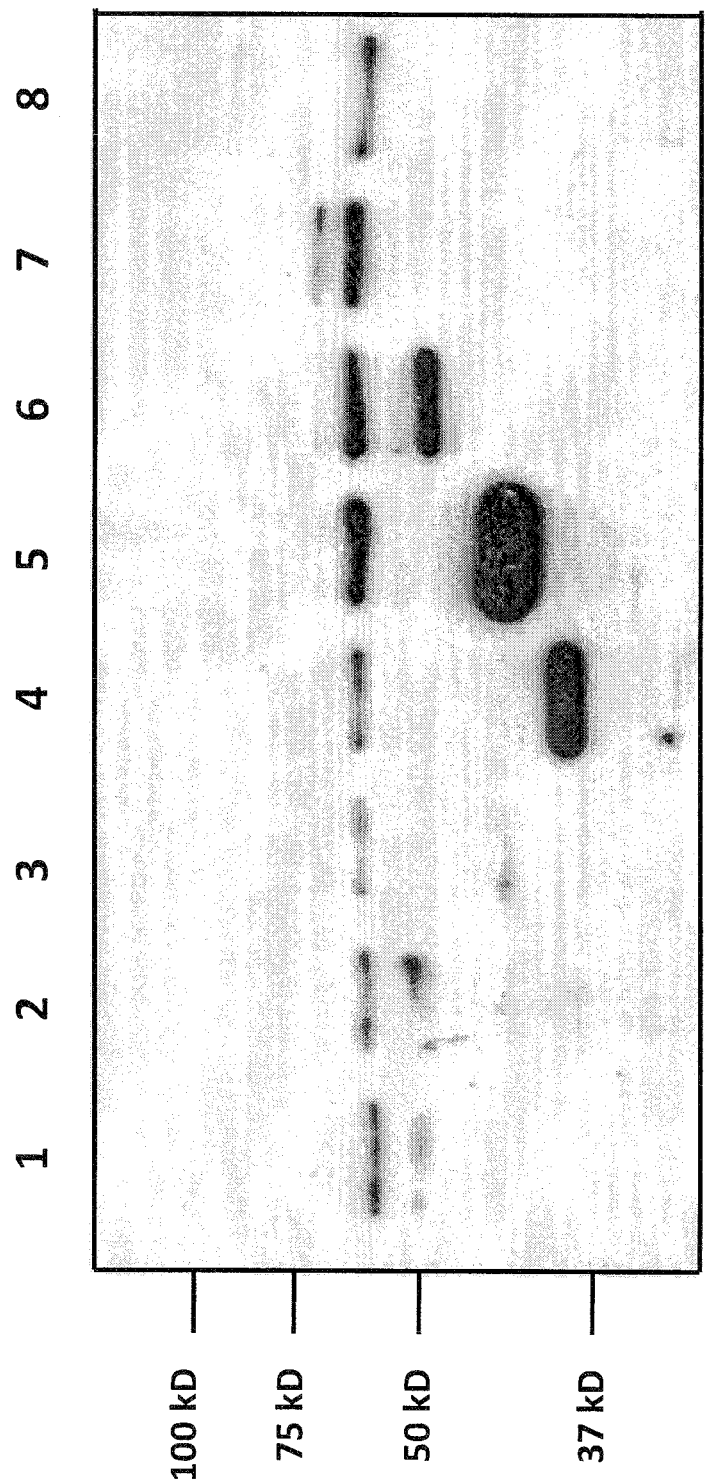
FIG. 8C. The strains were further tested for the fusion protein injection into Te26 cell. N, no infection control; V, vector control, PAK-JΔSTY/pUCP20; P, T3SS mutant control, PAK-JΔpopD/pExoS54-Cre; lanes 1-5 same as FIG. 8B.

Next, a human sarcoma cell line (Te26) was infected with PAK-JΔSTY containing the various length Cre recombinase fusions at an MOI of 50 for 2 hours. Immediately after infection, cells were washed in PBS, collected by trypsinization and lysed by 0.25% Triton X-100 in PBS for Western blot analysis of injected Cre recombinase. The injection assay indicated that while the first 17 amino acids of ExoS appear to be sufficient, 54 amino acids more efficiently directed Cre recombinase for type III secretion (FIG. 8C). Secretion was gradually reduced as the ExoS portion increased beyond 54 amino acids long. Given ExoS has a molecular weight of 48 kD, larger fusion constructs may not be as effectively translocated. To verify that ExoS54-Cre injection occurs in a type III specific manner, this construct was also expressed in a type III defective strain, PAK-JΔpopD, with no intracellular Cre recombinase upon Te26 infection (FIG. 8C) observed.

Functional Analysis of Bacterially Delivered Cre Recombinase.

Figure 9A:
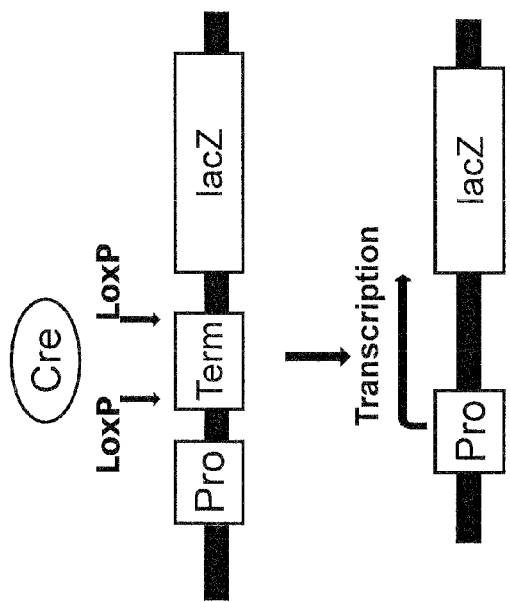
FIG. 9A. Cre function was assessed as a measure of β-galactosidase activity in Te26 cells which contain a foxed terminator preventing lacZ expression.

Having successfully injected ExoS54-Cre into Te26 cells, the question was whether or not it retained recombinase activity, as the N-terminal fusion of ExoS54 could potentially interfere with protein folding or function. To assess the functionality of the fusion protein, the Te26 cell line was employed, which contains a floxed SV40 transcriptional terminator that prevents downstream lacZ expression (FIG. 9A). Upon Cre mediated recombination, the DNA between the loxP sites was removed, allowing lacZ expression to be evaluated as β-galactosidase activity.

Figure 9B:
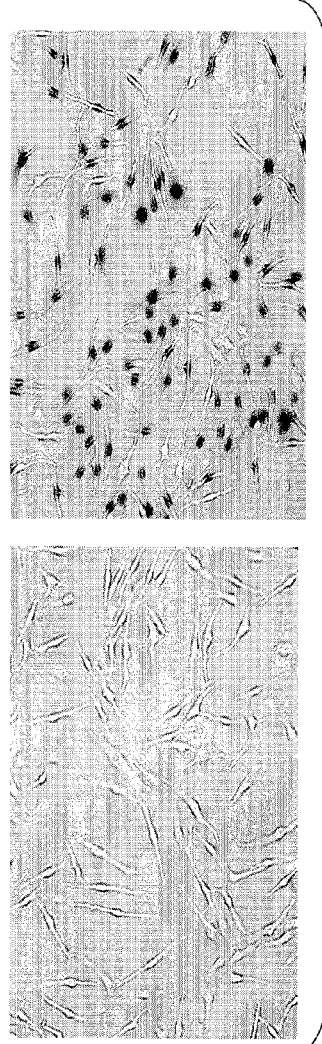
FIG. 9B. Te26 cells were infected for various times and MOIs and subsequently stained with X-gal.
Figure 9C:
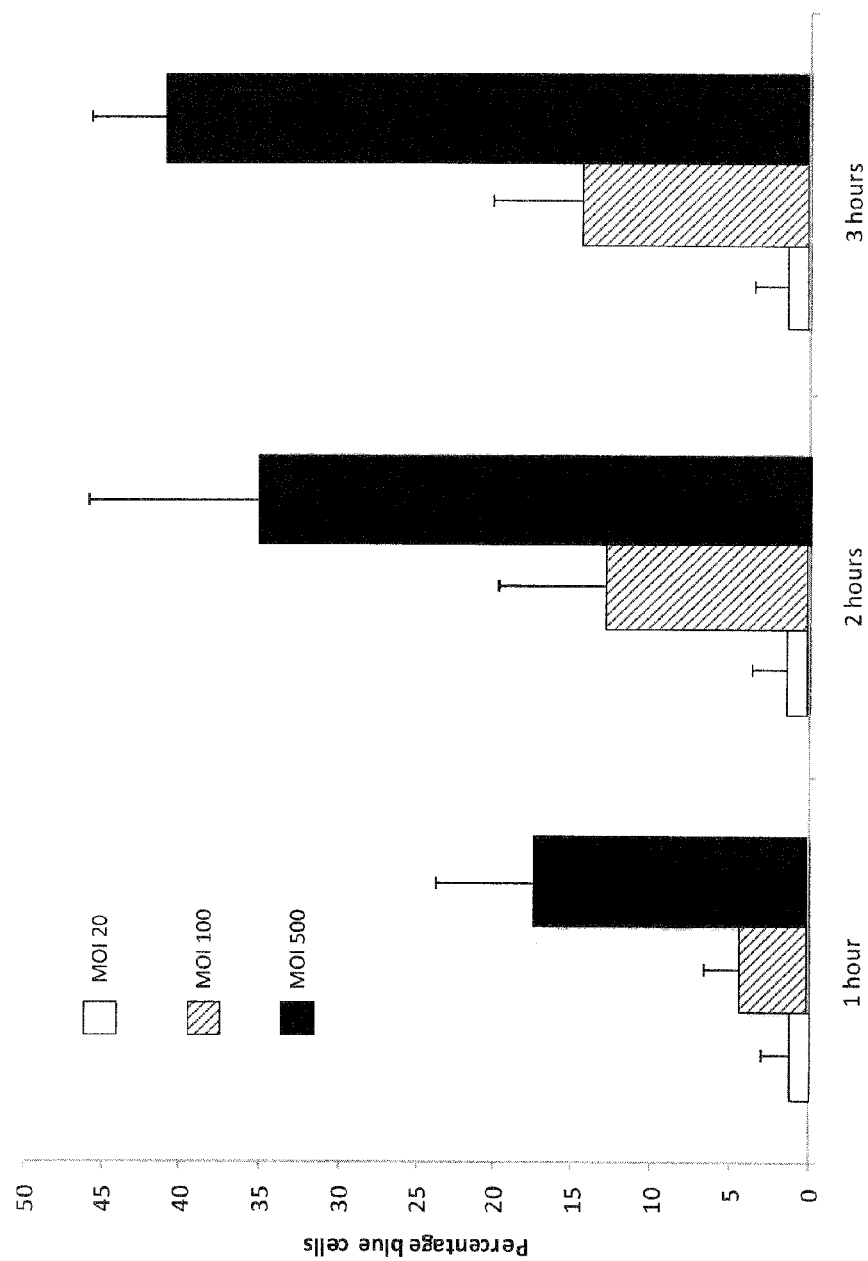
FIG. 9C. Optimal infection conditions indicated by percentage LacZ positive cells.

Te26 cells were infected with PAK-JΔSTY (pExoS54-Cre) at various MOIs (20, 100, 500) for 1-3 hours. The infections were cleared and cells were allowed 48 hours to undergo recombination and lacZ expression. Cells were then fixed and stained with a solution containing bromo-chloro-indolyl-galactopyranoside (X-gal) to assess β-galactosidase mediated cleavage of the substrate, generating an insoluble blue dye that stains the Te26 cells. After 24 hours of staining at 37° C., cells were visually counted using a light microscope to determine the percentage of cells which had undergone Cre-mediated recombination. As the lacZ reporter gene contains a nuclear localization sequence, the β-galactosidase activity was mainly observed inside the Te26 nuclei (FIG. 9B). The percentage of β-galactosidase positive cells increases in a dose and time dependent manner, with infection at an MOI of 500 for 3 hours resulting in the highest (42%) efficiency (FIG. 9C). The ability of bacterially delivered ExoS54-Cre to induce such levels of recombination indicates that the process of type III secretion and the presence of the ExoS54 signal sequence interfere with neither the biological function nor the nuclear localization of Cre recombinase.

Effect of Cell Cycle on the Efficiency of Cre Mediated Recombination.

Theoretically, for the Cre protein to mediate chromosomal DNA recombination, the two target loxP sites need to be freely accessible by Cre, which is most likely to occur during S phase of cell cycle. Indeed, the maximal 42% LacZ positive cells observed following infection of the Te26 cells correlated with 47% of S phase cells in the cell population, where G1/G0 and G2/M phase cells were 34% and 19%, respectively, as determined by FACS analysis of PI stained cells (FIG. 10). To test this further, Te26 cells were synchronized by a double thymidine blocking method. With the double thymidine treatment, 78% of the Te26 cells synchronized to S phase while G1/G0 and G2/M phase cells were 17% and 5%, respectively. Infection of the synchronized cells with the PAK-JΔSTY (pExoS-Cre) for 3 hours at an MOI 20 resulted in 75% LacZ positive cells (FIG. 10). The proportion of lacZ positive cells increased with the increased number of cells in S phase, thus the Cre mediated recombination is significantly influenced by the chromosome structure or cell cycle phase.

Delivery of Functional Nuclear Proteins to mESC.

Figure 11B:
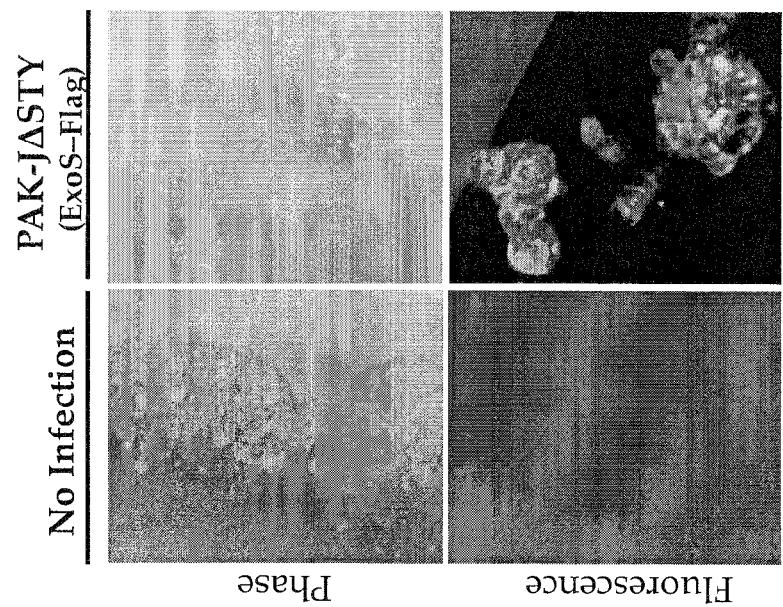
FIG. 11B. mESC were infected with PAK-JΔSTY (pExoS-Flag) for 2.5 hours and subsequently fixed and immunostained with anti-Flag to illuminate translocated ExoS-Flag protein.
Figure 11A:
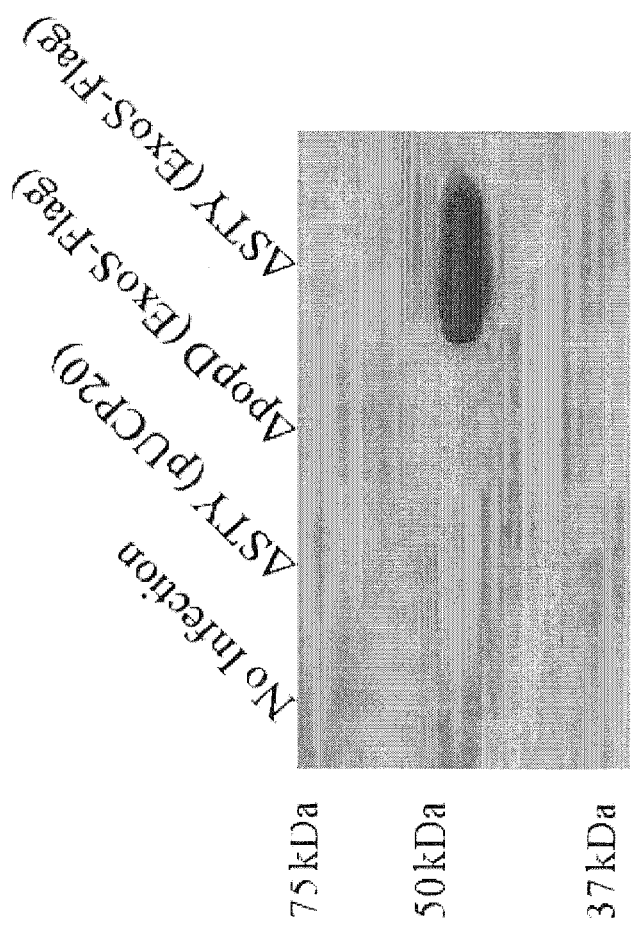
FIG. 11A. Susceptibility of mESC to *P. aeruginosa* infection is shown in FIGS. 11A-E. mESC were infected with PAK-J strains at a MOI of 100 for 2.5 hours, lysed and assayed for injected ExoS-Flag by anti-Flag Western Blotting.

Given the rise in the use of stem cells in many fields of biological and pharmaceutical research, a proficient protein delivery system should be applicable to both differentiated and pluripotent cells. While the ability of *P. aeruginosa* to infect an assortment of cell types in vitro has been well established, the susceptibility of pluripotent stem cells to *P. aeruginosa* infection was undetermined. In confirmation, mESC were infected with PAK-JΔSTY (pExoS-Flag), which expresses a catalytically inactive, Flag-tagged version of ExoS. Subsequent Western blot of the cell lysate illustrated clearly translocated ExoS-Flag (FIG. 11A). The translocation occurred in a type III secretion dependent manner as PAK-JΔpopD (pExoS-Flag), which is defective in type III secretion, was unable to deliver ExoS-Flag. These results are further substantiated by immunocytochemical staining of PAK-JΔSTY (pExoS-Flag) infected mESC with an anti-Flag antibody (FIG. 11B). Together these data suggested that mESC are also receptive to *P. aeruginosa* mediated protein delivery.

Figure 11C:
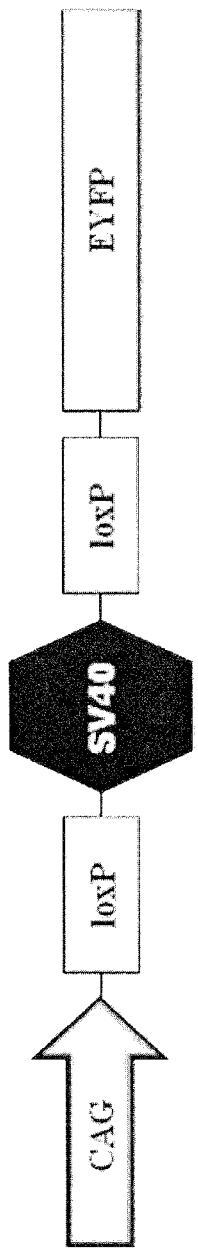
FIG. 11C. R26R-EYFP mESC cells contain a foxed terminator preventing downstream EYFP expression.
Figure 11D:
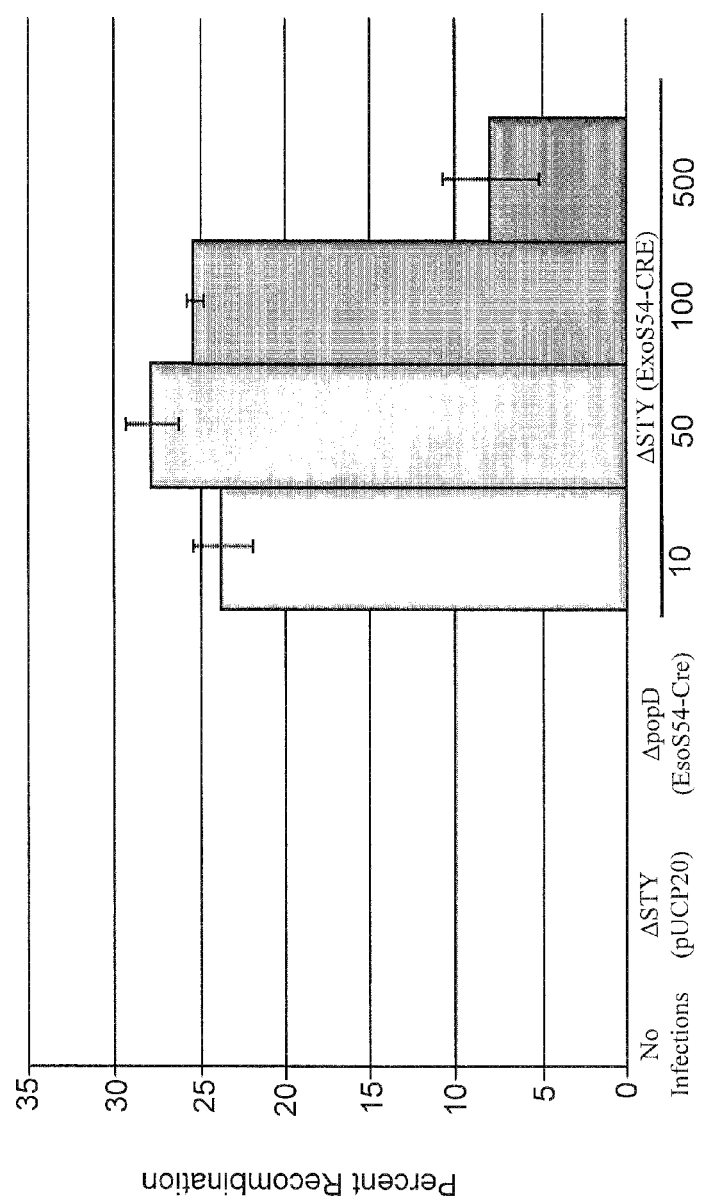
FIG. 11D. R26R-EYFP were infected with PAK-JΔSTY (pExoS54-Cre) at various MOIs for 2.5 hours. 48 hours post infection, cells were collected for flow cytometric analysis.
Figure 11E:
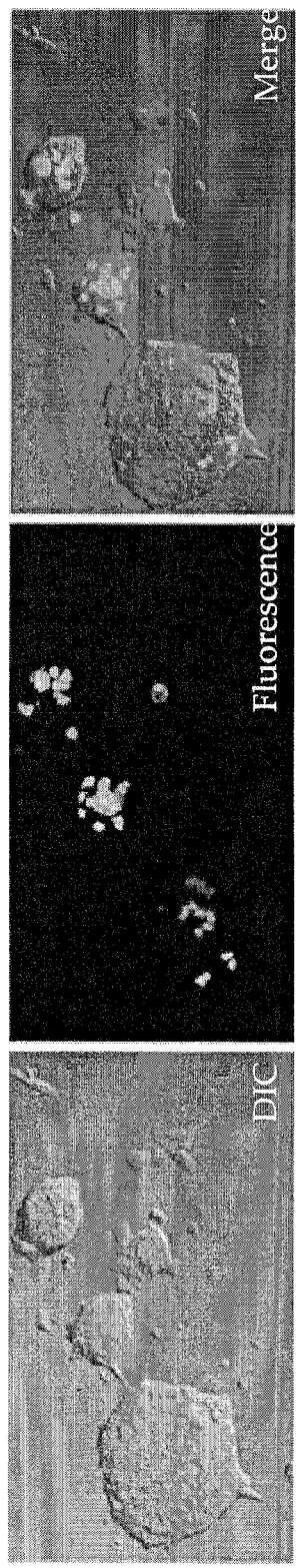
FIG. 11E. EYFP-positive mESC were plated after infection to assess EYFP expression by confocal fluorescence microscopy.

Considering the notorious difficulty of genetic manipulation in stem cells, it was not known whether or not type III secreted proteins would be able to localize to the mESC nucleus and maintain function. To quantitatively evaluate the functionality and efficiency of protein delivery to mESC, a reporter cell line, R26R-EYFP mESC, was used which contains a foxed SV40 terminator preventing downstream expression of Enhanced Yellow Fluorescent Protein (EYFP) in the *Rosa*26 locus (FIG. 11C). Similar to the Te26 reporter, Cre mediated recombination permits EYFP expression which can be visualized by fluorescence microscopy and quantified by flow cytometric analysis. R26R-EYFP mESC were co-incubated with PAK-JΔSTY (pExoS54-Cre) at various MOIs for 2.5 hours, as this duration was determined optimal in preliminary trials (data not shown). Cells were subjected to FACS analysis 48 hours post-infection. The efficacy of ExoS54-Cre mediated recombination is represented as the percentage of EYFP positive cells in the infected mESC population (FIG. 11D). Similar to the Te26 results, PAK-JΔSTY (pExoS54-Cre) induced recombination occurs in a type III secretion specific, dose dependent manner. Recombination efficiency peaks with an MOI of 50, resulting in nearly 30% EYFP positive cells, and steadily declines at higher MOIs, possibly due to increased cytotoxicity. After sorting, EYFP positive cells were plated on gelatin coated glass coverslips for observation of EYFP expression as well as cellular morphology (FIG. 11E). The ability of these previously infected cells to form colonies characteristic of mESCs and maintain similar growth rate demonstrated that neither bacterial infection nor bacterial protein mediated alteration in gene expression had significant effects on the pluripotency of these exceptionally sensitive cells.

Excision of Exogenous Reprogramming Genes from iPSC by Bacterial ExoS54-Cre.

Others have shown that induced pluripotent stem cells (iPSC) have been generated by forced expression of the transcription factors Oct4, Sox2, c-Myc, and Klf4, which are upregulated in embryonic stem cells. Exogenous expression of these factors activates stable expression of the endogenous pluripotency genes, relinquishing transgene dependency. While nuclear reprogramming is an important step in the field of stem cell biology, it is primarily criticized for the lingering oncogenic transgenes that remain integrated in the chromosome of iPSC.

Figure 12A:
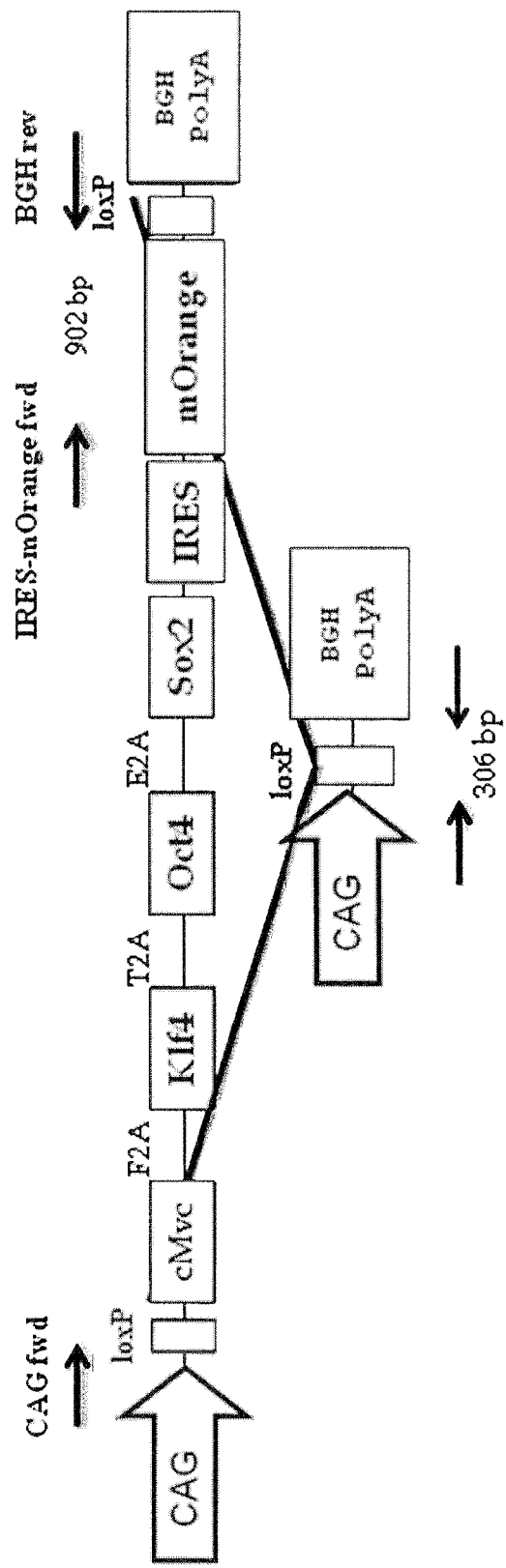
FIG. 12A. ExoS54-Cre mediated excision of an iPSC nuclear reprogramming cassette is shown in FIGS. 12A-D. TNGim05 iPSC contain a foxed reprogramming cassette.

In order to circumvent this issue, a nuclear reprogramming cassette was developed to contain all four transcription factors and a mOrange fluorescent reporter flanked by loxP sites (FIG. 12A), such that the cassette could be removed by Cre mediated recombination following stable reprogramming. TNGim05 mouse embryonic fibroblast derived iPSC were generated by integration of the single reprogramming cassette. As such, these cells display mESC-like morphology and mOrange expression when cultured in vitro. Upon recombination, it was anticipated that the reprogramming cassette would be excised, and the iPSC will maintain pluripotency, but lose mOrange expression.

Summary and Discussion of Bacterial Mediated Delivery of Proteins into Differentiated and Undifferential Cells The use of the bacterial type III secretion system for transient delivery of nuclear proteins to modify intrinsic gene expression has the potential to replace many of the current methods that have several pitfalls such as inefficient, mutagenic and clinically inapplicable. The utility of this system was shown using a strain of *P. aeruginosa* with diminished cytotoxicity to deliver Cre, a well characterized protein which functions only in the nucleus to interact with DNA and exerts its recombinase activity was generated. The availability of numerous Cre-dependent reporters was taken advantage of to observe the effects of Cre delivery to both differentiated and pluripotent cells. The ability of bacterially delivered ExoS54-Cre to induce high levels of β-galactosidase activity in Te26 cells indicated that the process of type III secretion and the presence of the ExoS54 signal sequence do not interfere with the ability of this protein to properly localize to the nucleus of host cells or exert its biological function.

Based on immunocytochemical staining of the translocated proteins, nearly 100% of cells were injected by the bacterially delivered proteins although the recombination efficiency never reached 100%. It is possible that Cre-mediated DNA recombination can only occur when the target loxP sites are freely available, most likely during the DNA replication in S phase. This is supported by a direct proportion of LacZ positive recombinant cells to the increased number of the S phase cells during infection. For Te26 cells, one full cell cycle takes around 34 hours to complete under our culture conditions and a transition time from G2 to S phase takes about 20 hours, thus to achieve close to 100% efficiency of recombination, the injected Cre protein needs to be stable for a time period when all the cells go through the S phase, which is at least 20 hours for Te26 cell (G2 to S phase). It is believed that one could achieve 100% Cre-mediated recombination by combining several approaches, including (i) an increase of S-phase cell fraction by synchronization, (ii) an increase of the half life of the translocated Cre by utilizing a proteosome inhibitor, and (iii) successive infections for catching S phase for every cell in the population.

While embryonic stem cells are notoriously sensitive, the presence of EYFP positive colonies after bacterial delivery of ExoS54-Cre indicates that these cells are susceptible to *P. aeruginosa* infection, but neither infection nor protein delivery significantly affects the pluripotency of R26R-EYFP mESCs. Given the inherent difficulty of manipulating embryonic stem cells, the present work demonstrates a relatively high delivery efficiency in a short time (2-3 hours) with a single infection. The infection efficiency can further be increased with multiple rounds of protein delivery.

A dose-dependent increase in the efficiency of ExoS54-Cre-mediated recombination was observed, which peaked around 30% at a MOI of 50 for R26R-EYFP mESC. The subsequent decline in recombination is may not be due to insufficient protein delivery, but more likely resultant of excess protein translocation or bacterial cytotoxicity. The deletion of the *P. aeruginosa* type III secreted exotoxins resulted in a considerable decrease in cytotoxicity, as compared to the wild-type PAK-J strain, which allowed cells to remain viable and undergo gene expression changes after infection. However, *P. aeruginosa* possesses additional virulence factors that contribute to cytotoxicity Currently, gentamicin and ciprofloxacin are used to eradicate any residual bacteria after infection. While bacterial survival assays have indicated that these conditions are sufficient to destroy lingering intracellular and extracellular bacteria (data not shown), it will be more convenient to infect with a strain that is sensitive to antibiotics commonly used in cell culture, such as penicillin and streptomycin. Alternatively, an auxotrophic mutant can also be utilized in which specific nutrient withdrawal results in killing of the remaining bacterial cells.

EXAMPLES

Materials and Methods

Table 1 is a list of the strains and plasmids used in some of the work reported herein. The material was obtainable by methods known in the art or, as described in some of the examples, prepared by the techniques described.

TABLE 1

Strains and plasmids

| Strain or plasmid | Description |
|---|---|
| *P. aeruginosa* | |
| PAO1 | *P. aeruginosa* laboratory strain |
| PAK | *P. aeruginosa* laboratory strain |
| PAK-J | PAK derivative with enhanced T3SS |
| PAKΔpopD | PAK with chromosomal deletion of the popD locus |
| PAKΔSTY | PAK with chromosomal deletion of exoS, exoT, exoY loci |
| *E. coli* | |
| S-17 | Strain expressing DNA mobilization genes |
| DH5α | F$^-$ φ80δlacZDM15 endA1 recA1 hsdR17(m$_k$-m$_k$-) supE44 thi-1 relA1 Δ(lacZYA-argF) gyrA96 deoR |
| Plasmids | |
| pUCP20 | *Escherichia-Pseudomonas* shuttle vector; Ap$^r$ (Cb$^r$) |
| pExoS17-Cre | 17 aa of ExoS fused to nuclear Cre recombinase in pUCP20; Cb$^r$ |
| pExoS54-Cre | 54 aa of ExoS fused to nuclear Cre recombinase in pUCP20; Cb$^r$ |
| pExoS96-Cre | 96 aa of ExoS fused to nuclear Cre recombinase in pUCP20; Cb$^r$ |
| pExoS234-Cre | 234 aa of ExoS fused to nuclear Cre recombinase in pUCP20; Cb$^r$ |
| pTYF-Cre | Cre gene clone in lentiviral vector |
| pExoS-Flag | pHW0224, pUCP18 containing catalytically inactive ExoS with a Flag tag; Cb$^r$ |
| pEX18Tc | Vector containing sacB and Tc$^r$ for exconjugant selection |
| pEX18Tc-ΔS | pEX18Tc containing 1kb regions up and downstream of exoS; Tc$^r$ |
| pEX18Tc-ΔT | pEX18Tc containing 1kb regions up and downstream of exoT; Tc$^r$ |
| pEX18Tc-ΔY | pEX18Tc containing 1kb regions up and downstream of exoY; Tc$^r$ |

Bacterial Strains and Plasmids.

The bacterial strains and plasmids used in this study are listed in Table 1. *P. aeruginosa* and *E. coli* were grown in Luria (L) broth or on L agar plates at 37° C. Antibiotics were used at a final concentration of 150 μg carbenicillin, or 100 μg tetracycline per ml for *P. aeruginosa* and 100 μg ampicillin per ml for *E. coli*.

Cell Culture.

Te26 cells were grown in Dulbecco's Modified Eagle Medium (DMEM; Gibco) supplemented with 15% Fetal Bovine Serum (FBS). R26R-EYFP mouse embryonic stem cells (mESC) and TNGim05 induced pluripotent stem cells (iPSC), were grown on 0.1% gelatin (Millipore) coated plates in mESC media. All cells were cultured at 37° C. with 5% $CO_2$, and supplemented with Penicillin, Streptomycin, and Amphotericin (Cellgro). Gentamicin and Ciprofloxacin were added at final concentrations of 200 μg and 20 μg per ml, respectively, where noted.

*P. Aeruginosa* Type III Secretion Assay.

Bacterial strains were grown overnight at 37° C. in L broth containing 150 μg carbenicillin per ml. Prior to infection, strains were subcultured at 5% (v/v) into fresh L broth containing carbenicillin and 5 mM EGTA to induce type III secretion. After 3 hours, 1.5 mL of the cultures were collected and centrifuged at 16,000 g for 2 minutes to remove bacterial cells. One ml supernatant was taken from each culture and precipitated with 0.2 ml trichloroacetic acid (TCA) on ice for 30 minutes. Samples were then centrifuged at 16,000 g for 10 minutes. The protein pellet fraction was washed in 0.2 ml acetone, and centrifuged for 5 minutes at 16,000 g. The pellet samples were allowed to dry for 10 minutes prior to addition of 1×SDS-PAGE loading buffer and boiling for 10 minutes. The secreted protein samples were then subjected to SDS-PAGE and Western blot analysis.

Protein Injection Assay.

Mammalian cells were plated at approximately 60% confluency in antibiotic-free media the night before infection. *P. aeruginosa* was grown at 37° C. in L broth containing carbenicillin until reaching $OD_{600}$ of 0.8. Cells were infected with $0.5 \times 10^8$ cfu *P. aeruginosa* per ml of growth media for a multiplicity of infection (MOI) of 50. Cells were co-incubated with *P. aeruginosa* for 3 hours in DMEM containing 5% FBS, unless otherwise stated. Infections were cleared by removing the media and washing cells 3 times in PBS, and adding media containing gentamicin and ciprofloxacin.

For Western Blot analysis of translocated proteins, cells were collected immediately following infection by incubation with 0.25% Trypsin (CellGro) for 5 minutes. The suspension was centrifuged for 5 minutes at 500 g. Cells were washed in PBS, and centrifuged for 5 minutes at 500 g. The cell pellets were lysed in 400 PBS containing 0.25% Triton-X on ice for 10 minutes. The lysed cells were then centrifuged at 16,000 g for 5 minutes. The soluble fraction was collected, mixed with an equal volume of 2×SDS-PAGE loading buffer and boiled for 10 minutes.

Western blot analysis.

Prepared samples were subjected to electrophoresis on 12% SDS-PAGE and transferred to PVDF. Blots were blocked with 5% non-fat dry milk in PBST (PBS with 0.1% Tween20) and probed with antibodies against ExoS (rabbit polyclonal), Cre recombinase (mouse monoclonal, Abcam), or Flag (mouse M2 monoclonal Ab, Sigma). Following incubation with HRP conjugated secondary antibodies, light signal was generated by chemoluminecent reagents (GE Health Science) and detected by exposure to X-ray film.

Immunocytochemistry.

Cells were fixed in 3.7% formaldehyde in PBS for 15 minutes at room temperature. Cells were then washed 3× in PBS and permeablized in 0.5% Triton X-100 in PBS. Cells were then washed 3× in PBST and blocked with 1% BSA in PBST for 30 minutes. Cells were incubated with primary antibodies for 2 hours at room temperature, then washed 3× in PBST. Cells were incubated with the secondary antibody for 1 hour at room temperature, then washed 3× in PBST and examined under fluorescence microscope.

Cytotoxicity Assays.

Cells were infected by *P. aeruginosa* for 1, 2, or 3 hours as described above. After infection, the cells were washed and incubated in antibiotic containing media for overnight. Approximately 24 hours after infection, 0.2 ml media samples were taken from each condition to quantify LDH release using CytoTox96 (Promega). The percentage of LDH released was determined using uninfected, lysed cells as 100% and uninfected, intact cells as 0% LDH release. After collecting samples for LDH analysis, the remaining media was aspirated from the wells and stained with 0.5% Crystal Violet. After 10 minutes, the excess crystal violet was removed by repeated submersion in water. The stained plates were allowed to dry and destained in 1 ml 95% EtOH. Samples were then collected for colorimetric analysis at 495 nm.

β-Galactosidase Assays.

Te26 cells were stained for β-galactosidase activity 48 hours after *P. aeruginosa* infection. Cells were fixed in 1% formaldehyde and 0.2% gluteraldehyde in PBS for 5 minutes and stained in a solution containing 4 mM $K_4Fe(CN)_6$, 4 mM $K_3Fe(CN)_6$, 2 mM $MgCl_2$ and 0.4 mg/ml X-gal for 24 hours at 37° C. Percent β-galactosidase positive cells were determined by visual counts of blue and white cells under a light microscope.

Flow Cytometry.

Infected cells were collected by 0.25% Trypsin treatment 48 hours after *P. aeruginosa* infection. Cells were centrifuged at 500 g for 5 minutes and resuspended in 0.5 ml PBS containing 2% FBS. Cells were analyzed for EYFP or mOrange expression using Diva v6.2 on LSR-II (BD-Biosciences) for flow cytometry and FACS Aria II (BD-Biosciences) for fluorescence associated cell sorting (FACS).

Cell Synchronization.

Te26 cells grown in DMEM containing 15% FBS were cultured for 2 days and then incubated in medium containing 2 mM thymidine for 18 hours. Cells were then washed twice with PBS, and incubated with regular DMEM for 9 hours before a second incubation in 2 mM thymidine for 17 hours. At 0, 2, 5, 6, 9, 12, 16 and 24 hours after release from the second thymidine block, cell-cycle phase distribution was analyzed by flow cytometry with propidium iodide (PI) staining to verify the synchrony. Briefly, cells were fixed with ice-cold 70% ethanol for 24 h, then centrifuged and the cell pellet resuspended in 0.4 ml of PBS, 50 μl of RNase A (10 mg/ml) and 10 μl of PI (2 mg/ml). The mixture was incubated in the dark at 37° C. for 30 min and then analyzed by FACsort flow cytometer (Becton Dickinson).

Fluorescence Microscopy.

Cells for examination by fluorescence microscopy were grown on 0.1% gelatin coated glass coverslips. Immediately prior to analysis, coverslips were coated in VectaShield and mounted. Fluorescence was detected using Leica Confocal Software v2.61, on the Leica TCS SP2AOBS Spectral Confocal Microscope, by Leica Microsystems (Heidelberg GmbH).

Example 1

Mutant Strain PAKΔexoSTY

Virulence determinants of *P. aeruginosa* include toxins encoded on the exoenzyme S regulon. Three effector proteins of the ExoS regulon include ExoS, ExoT and ExoY (Yahr, et al., 1998). Using standing deletion procedures, Exo S, Exo T and ExoY encoding regions were deleted.

To minimize killing of the host cells, a mutant strain, PAK-ΔexoSTY, deleted of all three T3SS-dependent cytotoxins (exoS, exoT and exoY), was generated. Growth rate of the resulting strain is identical to that of wild type strain PAK. By a standard cytotoxicity assay (LDH release assay), the mutant strain lost more than 80% of its cytotoxicity toward MEF cells in a 3 hour infection assay (MOI 100) and displayed almost no cytotoxicity under the test condition of MOI 100 with one hour infection time.

To delete the three virulence genes, allelic exchange technique was utilized. For each gene, 1 kb fragments from upstream and downstream of the target coding gene were amplified by PCR, utilizing primers listed in the Table 2, i.e., primers SEQ ID NO. 1 and SEQ ID NO. 2 for ExoS upstream, primers SEQ ID NO. 3 and SEQ ID NO. 4 for ExoS downstream; primers SEQ ID NO:5 and SEQ ID NO:6 for ExoT upstream, primers SEQ ID NO:7 and SEQ ID NO:8 for ExoT downstream, SEQ ID NO. 9 and SEQ ID NO:10 for ExoY upstream and SEQ ID NO:11 and SEQ ID NO:12 for ExoY downstream. In all cases, primers for the upstream fragment introduced EcoRI and BamHI or BglII restriction sites at 5' and 3' ends, respectively, while the downstream fragments introduced BamHI or BglII and HindIII restriction sites at 5' and 3' ends, respectively. The PCR amplified upstream fragments were digested with EcoRI and BamHI or BglII restriction enzymes while down stream fragments were digested with BamHI or BglII and HindIII restriction enzymes. Corresponding up- and down-stream fragments were ligated with pEX18Tc vector that was digested with EcoRI and HindIII. Resulting ligation constructs had up- and down-stream fragment ligations, lacking the target genes. Each of the resulting constructs was sequenced to confirm proper deletion and introduced into an *E. coli* strain S17 by electroporation. The strain S17-encodes mobilization gene clusters (tra genes) for conjugation of oriT containing plasmids, such as pEX18Tc derivatives.

First, exoS deletion construct (pEX18Tc-ΔexoS) was introduced into a wild type *P. aeruginsoa* strain PAK by conjugation. Log phase bacterial cells (in L-broth) of the donor and recipient cells (total $9 \times 10^8$ cells) were mixed at 2:1 ratio on 0.45 μm nitrocellulose filter discs (R=3 cm) and placed on nutrient agar plate for overnight. Bacterial cells on the disc were washed off in l ml L-broth and plated 20 μl on L-agar plate containing 100 μg/ml tetracycline and 25 μg/ml kanamycin. Single colonies were picked and grown in 3 ml fresh L-broth without antibiotics for overnight. The culture was serially diluted in L-broth and plated on L-agar containing 5% sucrose. Single colonies were purified by streaking on the same plate and tested for double crossovers by PCR utilizing 5' primer for upstream fragment and 3' primer for the downstream fragment. Desired exoS deletion showed 2 kb PCR product while wild type PAK showed 3.5 kb fragment. The deletion mutant was further confirmed by the lack of ExoS protein secretion in a type III secretion assay.

For further deletion of the additional genes, the same protocol was followed, utilizing the previous deletion mutant as the start strain. Accordingly, for ExoS-Cre fusions, primers with SEQ ID NOs 13-21 were employed, as shown in Table 2.

TABLE 2

PCR primers used amplify up and down stream fragments of the target genes

| Fragments | 5' and 3' PCR primer sets |
|---|---|
| ExoS upstream (EcoR1-BglII) | 5'-CAAGgaATTCGGATTATGCGGAGGGGTTGCCGGTG-3' (SEQ ID NO: 1)<br>5'-GTTGagaTCTCCTGATGTTTCTCCGCCAGTCTAGGAA-3' (SEQ ID NO: 2) |
| ExoS downstream (BglII-HindIII) | 5'-GTCCagaTCTTGGCTCGGCAGCGGATCCGGGTGGAG-3' (SEQ ID NO: 3)<br>5'-TGGAaaGCTTCGTCATCCTCAATCCGTACGGCAGGC-3' (SEQ ID NO: 4) |
| ExoT upstream (EcoR1-BamH1) | 5'-GGAGgaaTTCGAAGGGGTTGCGCAGGCCTGGCTCGTC-3' (SEQ ID NO: 5)<br>5'-TGACggaTCCTGATGTTTCCCCGCCAGTCTAGGAACG-3' (SEQ ID NO: 6) |
| ExoT downstream (BamH1-HindIII) | 5'-CGGAggaTCCCAAGGGGTGTCCGTTTTCATTTGCGCC-3' (SEQ ID NO: 7)<br>5'-AGGTaaGCTTCCAGCGCCTGCGCCTGGGCCTCCTTG-3' (SEQ ID NO: 8) |
| ExoY upstream (EcoR1-BamH1) | 5'-AACTgaattCCGAGGATGTCGCCCTGCTCGACCATCGGG-3' (SEQ ID NO: 9)<br>5'-CCCAggaTCCAGGAGGCGCTCGACTTTTTCCAACGTA-3' (SEQ ID NO: 10) |
| ExoY downstream (BamH1-HindIII) | 5'-ATAAggATCCGGGCAGCGGCGAGATATCAGAAAACG-3' (SEQ ID NO: 11)<br>5'-CGTTaagCTTGAGATAGCCGAGCATGCTCAGGCCGTC-3' (SEQ ID NO: 12) |
| For ExoS-Cre fusions<br>ExoS-upstream | 5'-GACGAATTCGGCGTCTTCCGAGTCACTGGAGGC-3' SEQ ID NO: 13 |
| ExoS17 downstream | 5'-GACGAGTCGTGCAATTCGACGGCGAAAGACGG-3' SEQ ID NO: 14 |
| ExoS54 downstream | 5'-<u>GAGCTC</u>GAGCAGCCCCTCACCCTTCGGCGCGTCC-3' SEQ ID NO: 15 |
| ExoS96 downstream | 5'-GACGAGCTCGGACATCAGCGCAGGCTGCGCGTC-3' SEQ ID NO: 16 |
| ExoS129 downstream | 5'-GACGAGCTCTTCCGGTGTCAGGGTCGCCAGCTC-3' SEQ ID NO:17 |
| ExoS234 downstream | 5'-GACGAGCTCCTTGTCGGCCGATACTCTGCTGAC-3' SEQ ID NO: 18 |
| ExoS full downstream | 5'-GACGAGCTCGGCCAGATCAAGGCCGCGCATCCT-3' SEQ ID NO: 19 |
| Cre upstream | 5'-GGAGCTCATGCCTAAGAAGAAACGAAAGATC-3' SEQ ID NO: 20 |
| Cre downstream | 5'-CGAGGTCGACGGTATCGATAAGCTTG-3' SEQ ID NO: 21 |

Figure 2:
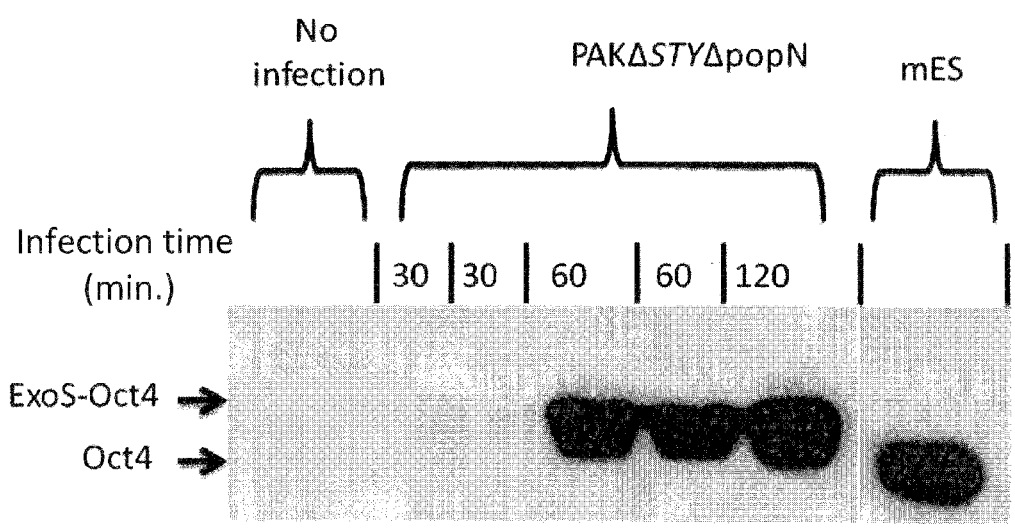
FIG. 2 shows injection of ExoS-Oct4 into MEF cells. MEFs were infected with *P. aeruginosa* at MOI 50 for the indicated time. Cytosolic extracts of the infected MEFs and mouse ES cells were subjected to Western blot using anti-Oct4 antibody.

The newly generated mutant strain (PAKΔexoSTY) was tested for the effector protein translocation into MEF cells. A stem cell specific transcriptional factor Oct4 was fused behind a 54 amino acid long secretion signal sequence from ExoS and tested for T3SS dependent injection into host cells. The plasmid expressing ExoS-Oct4 fusion was introduced into the mutant strain and the resulting strain was used to infect MEF at MOI 50 for 30, 60 and 120 minutes. MEF cells were selectively lysed by PBS containing 0.25% Triton X-100 which does not lyse the bacterial cells. Intact bacterial cells and cell debris were removed by centrifugation. Translocated ExoS-Oct4 protein was then detected by Western blot. As the results show (FIG. 2), the newly generated strain can effectively inject the ExoS-Oct4 protein into MEF, with maximal translocation within 120 minutes. Furthermore, the bacterial delivery of the ExoS-Oct4 is comparable to the endogenous Oct4 level in mouse ES cells (FIG. 2), indicating that a sufficient amount of protein was delivered by the bacteria.

To determine the percentage of MEF cells that were being injected of the type III effectors, MEF cells were subjected to infection by P. aeruginosa harboring ExoS tagged with Flag at the C-terminus. Following infection for 2 hours at MOI 20, 100% of the MEF cells were stained positive for the Flag-tag by immunostaining (FIG. 3), indicating an extremely high efficiency of protein delivery by the P. aeruginosa. As expected, translocated ExoS-Flag is highly enriched in the paranuclear membrane.

Example 2

T3SS Mediated Injection of Cre Recombinase

To assess functionality of proteins translocated by the T3SS, Cre recombinase was fused behind the ExoS signal sequence (54aa), and a nuclear targeting sequence (NLS) was added between them. The mutant *P. aeruginosa* strain harboring the ExoS54-Cre fusion construct was used to infect a reporter cell line TE26 (Chang, 2003). The TE26 is a human carcinoma derivative which harbors a lacZ reporter gene with NLS. However, its upstream promoter (EF1α) was interrupted by the SV40 transcriptional terminator which harbors a loxP site on each end (FIG. 4). Removal of the transcriptional terminator by Cre mediated recombination of the two loxP sites resulted in constitutive expression of the lacZ whose product localized into nucleus due to the presence of NLS.

Reporter cells were infected with the bacteria, washed to remove excess bacteria and grown in DMEM+15% FBS plus antibiotics for 48 hours to allow the expression of the reporter gene. The β-galactosidase positive cells appeared in a dose and time dependent manner whereas no blue colored cell was observed in an uninfected control. After two hours of infection at MOI 100, as high as 75% of the cells became positive for the β-galactosidase (FIG. 4). These results clearly demonstrated that the *P. aeruginosa* can deliver a high level of ExoS54-Cre protein which not only targets to nucleus but also retains its biological function.

Example 3

T3SS can Effectively Inject Effector Protein into ES Cells

Mouse ES cells were further tested for T3SS dependent protein injection. Two day old R1 ES cells were infected with the mutant *P. aeruginosa* strain PAKΔexoSTY harboring a plasmid encoding ExoS-FLAG fusion. The plasmid encoded ExoS had two point mutations which knocked out both GAP and ADP-ribosyltransferase activity, thus rendering it non-cytotoxic to the host cells. After two hours of co-culture at MOI 100, excess bacterial cells were washed off and the ES cells were subjected to immunohistochemistry staining for the translocated ExoS-FLAG using anti-FLAG monoclonal antibody.

Figure 5:
FIG. 5 shows infection of ES cells by *P. aeruginosa*. R1 mouse ES cells were incubated with PAKΔSTY (pExoS-Flag) at an MOI of 100 for two hours. Cells were then fixed and stained with mouse anti-Flag followed by anti-mouse fluorescein Ab.

As the images of immunohistochemistry show in FIG. 5, injected ExoS-FLAG protein is observed among majority of those subjected to the bacterial infection while ES cells without the bacterial infection showed no sign of ExoS-FLAG injection. Furthermore, the injected ExoS-FLAG localized within the cytoplasmic space, consistent with similar observations in non-ES cells. Therefore, it is clear that T3SS mediated protein delivery system is highly effective in injecting effector molecules directly into the ES cells.

ES cells were quite resistant to *P. aeruginosa* infection, as indicated by no obvious cell killing even at MOI 1,000 for 2 hours of incubation. This makes it possible to subject the ES cells to high MOI and/or multiple rounds of protein injection to achieve extremely high levels of intracellular proteins for a desired period of time.

Example 4

ExoS-Oct4 is Functional

To test if the ExoS-Oct4 fusion is functional, a retroviral vector expressing ExoS-Oct4 was constructed. In a standard iPS inducing protocol, MEF cells were infected with retrovirus expressing the four reprogramming factors where the Oct4-expressing retrovirus was replaced with that of ExoS-Oct4. iPS-like colonies appeared after day 13 at a similar rate as when conventional four factors were used. Majority of the colonies were positive for alkaline phosphatase (data not shown). Therefore, the ExoS-Oct4 is functional and can replace Oct4 to induce iPS cells.

Example 5

Bacteria Delivered Oct4 and Padx1 can Effectively Turn on their Respective Downstream Genes Functions of the bacterially delivered transcriptional factors were further analyzed. Transcriptional factors Oct4 and pdx1 were each fused behind the ExoS signal sequence and introduced into the *P. aeruginosa* mutant strain (ΔExoSTY). For Oct4, HeLa cells were transfected with a luciferase reporter plasmid driven by an Oct4-responsive promoter. 24 hours post transfection, the cells were further infected with the Oct4 delivery strain (MOI 20 for 2 hours). Bacterial cells were removed by washing and the HeLa cells were continuously cultured in the presence of antibiotics. Cells were then collected at various time points and cell lysates subjected to the standard luciferase assay (Promega assay kit). Compared to the non-infected cells, more than 8 fold luciferase activity was observed when the cell lysates were assayed 16 hours post bacterial infection.

Similarly, NIH 3T3 cells were infected with lentivirus coding for the luciferase reporter gene under the control of insulin responsive promoter. 24 hours post infection, the cells were incubated with *P. aeruginosa* harboring a plasmid encoding ExoS54-Pdx1 fusion. The infection was carried out at MOI of 20 for 2 hours. After clearing the bacteria as described above, cells were cultured for additional 16 hours before subjecting to the luciferase assay. Again, cells infected by the bacteria displayed more than 6-fold higher luciferase activity than the uninfected control cells.

Combining the above observations, it was concluded that the bacteria effectively deliver functional transcriptional factors which not only target to nuclei but also mediate the control of downstream gene expression.

Example 6

Cassette Excision

As demonstrated in R26R-EYFP mESC, PAK-JΔSTY (pExoS54-Cre) infection can induce recombination at considerable efficiency, without disrupting pluripotency. As such, the disclosed protein delivery system was expected to be applied to excise the floxed reprogramming cassette in the TNGim05 iPSC.

Figure 12B:
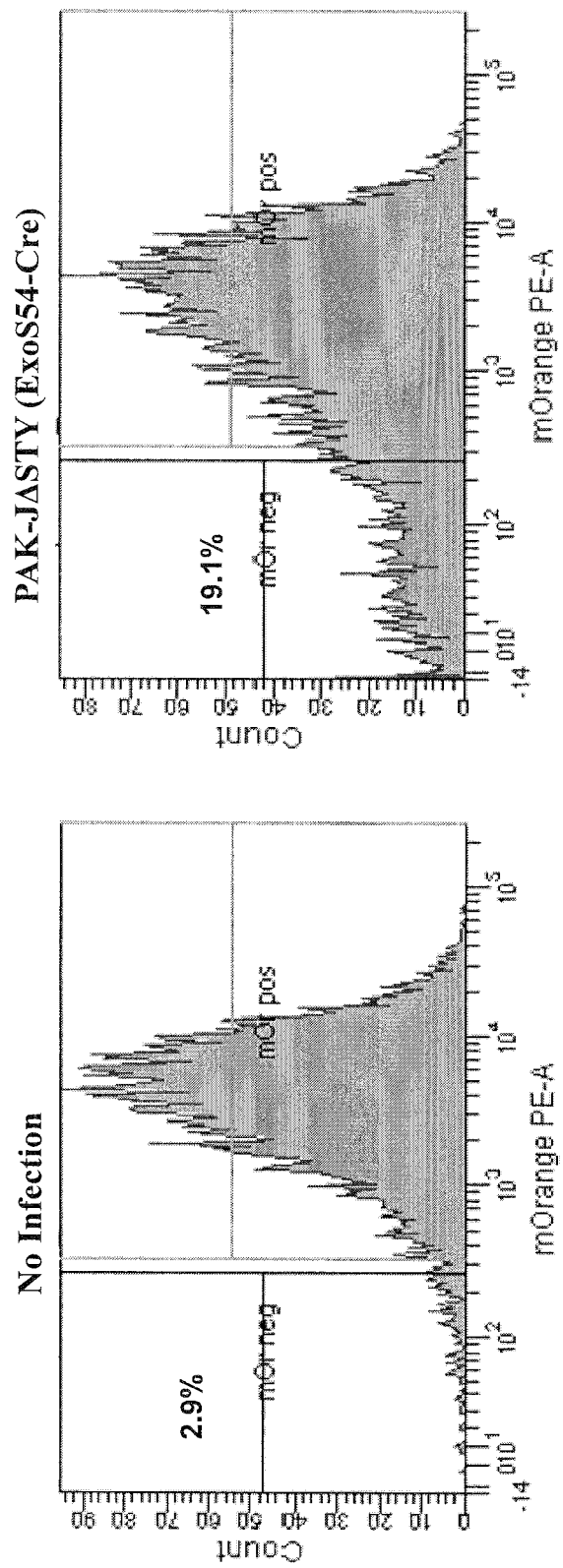
FIG. 12B. ExoS54-Cre mediated excision, TNGim05 cells lose mOrange expression. The efficiency of recombination after infection with PAK-JΔSTY (pExoS54-Cre) for 2.5 hours at an MOI of 50 was assessed by flow cytometric analysis for the decrease of mOrange-positive cells.
Figure 12C:
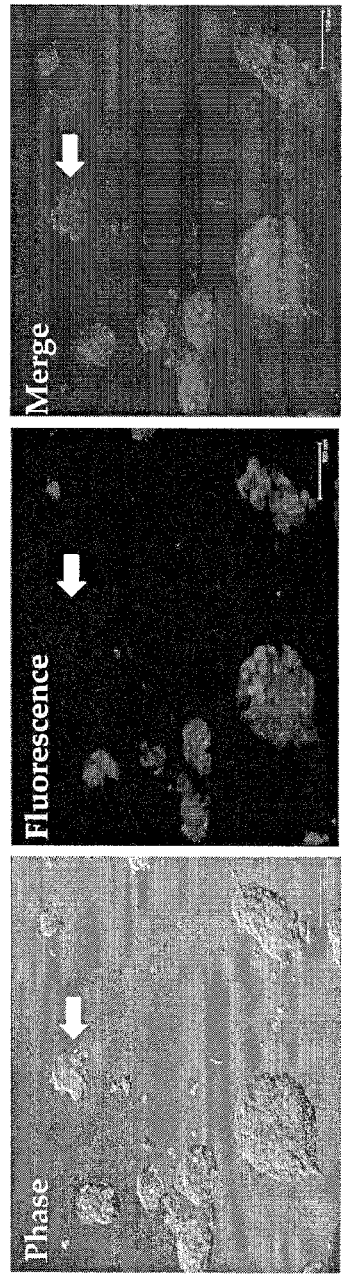
FIG. 12C. The mOrange negative population can also be visualized by fluorescence confocal microscopy and visualized by confocal microscopy.
Figure 12D:
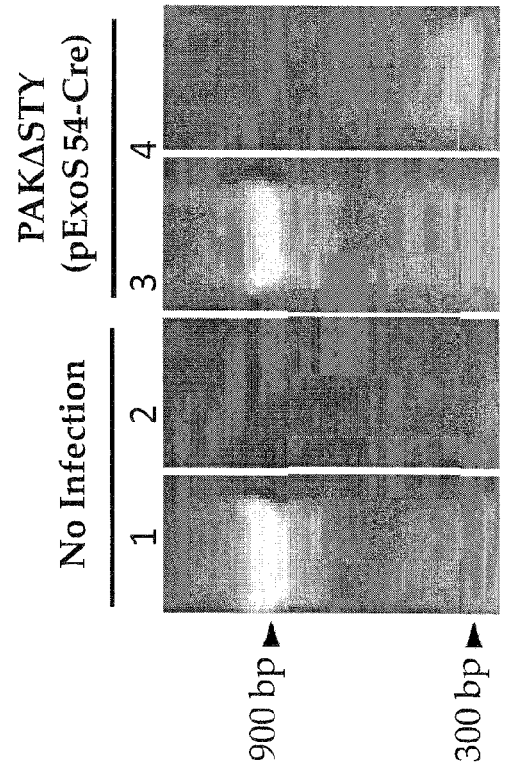
FIG. 12D. Lanes 1 and 3, IRES primer set, lanes 2 and 4, CAG primer set.

The TNGim05 iPSC were infected at an MOI of 50 for 2.5 hours, as this condition maximized ExoS54-Cre mediated recombination in R26R-EYFP mESC (FIG. 11D). Cells were allowed 48 hours to undergo recombination prior to FACS analysis. Sorted cells were evaluated for recombination as indicated by percentage of decrease in mOrange positive cells (FIG. 12B). While both infected and uninfected TNGim05 iPSC samples contain an mOrange negative population, there was a significant increase with PAK-JΔSTY (pExoS54-Cre) infection (FIG. 12C), indicating a subpopulation of the negative cells have actually undergone recombination. Cassette excision was verified by PCR analysis (FIG. 12D) of pooled mOrange negative TNGim05 iPSC cells. In congruence with the fluorescence microscopic imaging, PCR results demonstrate that while not the entire mOrange negative population underwent recombination, there was a substantial fraction of cells having had the reprogramming cassette removed in an ExoS54-Cre dependent manner.

Example 7

In Vivo Delivery of Bacterial ExoS54-Cre

Flox-lacZ mice will be infected with PAK-JΔSTY (pExoS54-Cre), prepared as described and administered as appropriate for the cell; e.g. liver, spleen and blood vessels can be biopsied after infection and stained to determine whether or not recombination had occurred; muscle can be stained at the site of an intramuscular (IM) injection. Other organs can be examined after administration, whether by IP, IM oral inhalation or other methods known in the art.

REFERENCES

Yu, J., M. A. Vodyanik, P. He, Slukvin, I I, and J. A. Thomson. 2006. Human embryonic stem cells reprogram myeloid precursors following cell-cell fusion. Stem Cells 24:168-76.

Takahashi, K., and S. Yamanaka. 2006. Induction of pluripotent stem cells from mouse embryonic and adult fibroblast cultures by defined factors. Cell 126:663-76.

Okita, K., T. Ichisaka, and S. Yamanaka. 2007. Generation of germline-competent induced pluripotent stem cells. Nature 448:313-7.

Yu, J., M. A. Vodyanik, K. Smuga-Otto, J. Antosiewicz-Bourget, J. L. Frane, S. Tian, J. Nie, G. A. Jonsdottir, V. Ruotti, R. Stewart, Slukvin, I I, and J. A. Thomson. 2007. Induced pluripotent stem cell lines derived from human somatic cells. Science 318:1917-20.

Takahashi, K., K. Tanabe, M. Ohnuki, M. Narita, T. Ichisaka, K. Tomoda, and S. Yamanaka. 2007. Induction of pluripotent stem cells from adult human fibroblasts by defined factors. Cell 131:861-72.

Hanna, J., M. Wernig, S. Markoulaki, C. W. Sun, A. Meissner, J. P. Cassady, C. Beard, T. Brambrink, L. C. Wu, T. M. Townes, and R. Jaenisch. 2007. Treatment of sickle cell anemia mouse model with Ips cells generated from autologous skin. Science 318:1920-3.

Nakagawa, M., M. Koyanagi, K. Tanabe, K. Takahashi, T. Ichisaka, T. Aoi, K. Okita, Y. Mochiduki, N. Takizawa, and S. Yamanaka. 2008. Generation of induced pluripotent stem cells without Myc from mouse and human fibroblasts. Nat Biotechnol 26:101-6.

Okita, K., M. Nakagawa, H. Hyenjong, T. Ichisaka, and S. Yamanaka. 2008. Generation of mouse induced pluripotent stem cells without viral vectors. Science 322:949-53.

Stadtfeld, M., M. Nagaya, J. Utikal, G. Weir, and K. Hochedlinger. 2008. Induced pluripotent stem cells generated without viral integration. Science 322:945-9.

Chauhan, A., A. Tikoo, A. K. Kapur, and M. Singh. 2007. The taming of the cell penetrating domain of the HIV Tat: myths and realities. J Control Release 117:148-62. Epub 2006 Nov. 17.

Keller, G. 2005. Embryonic stem cell differentiation: emergence of a new era in biology and medicine. Genes Dev 19:1129-55.

Ying, Q. L., M. Stavridis, D. Griffiths, M. Li, and A. Smith. 2003. Conversion of embryonic stem cells into neuroectodermal precursors in adherent monoculture. Nat Biotechnol 21:183-6. Epub 2003 Jan. 13.

Chang, L. J., and A. K. Zaiss. 2003. Self-inactivating lentiviral vectors and a sensitive Cre-loxP reporter system. Methods Mol Med 76:367-82.

Taranger, C. K., Noer, A. L., Sorensen, A. M., Hakelien, A. C., Boquest and Collas, 2005 Induction of dedifferentiation genomewide transcriptional programming and epigenetic reprogramming by extracts of carcinoma and embryonic stem cells, Mol. Biol. Cell 16:5719-35.

What is claimed is:

1. A method of delivering one or more nuclear proteins into one or more isolated cells, comprising:

incubating the cell or cells with a *Pseudomonas* bacteria deletion mutant lacking genes encoding ExoS, ExoT, and ExoY proteins, said deletion mutant comprising a plasmid or plasmids comprising nucleic acid sequences encoding one or more fusion proteins, wherein each nucleic acid sequence comprises a nucleic acid sequence encoding a nuclear protein fused to a nucleic acid sequence encoding the N-terminus of an ExoS protein or a nucleic acid sequence encoding a signal sequence from an ExoS protein, and the nucleic acid further comprises a nucleic acid sequence encoding a nuclear localization sequence between the nucleic acid sequence encoding the N-terminus of an ExoS protein or a nucleic acid sequence encoding a signal sequence from an ExoS protein and the nucleic acid sequence encoding the nuclear protein;

and incubating the isolated infected cell or cells for a period of time sufficient to deliver the one or more nuclear proteins into said cell or cells.

2. The method of claim 1 wherein the *Pseudomonas* is *P. aeruginosa; P. alcaligenes; P. anguilliseptica; P. citronello-* lis; *P. flavescens; P. jinjuensis; P. mendocina; P. nitroreducens; P. oleovorans; P. pseudoalcaligenes; P. resinovorans*; or *P. straminae*.

3. The method of claim 1 wherein the *Pseudomonas* is *P. aeruginosa*.

4. The method of claim 1 wherein the cell is a ROSA26-EYFP embryonic stem (ES) cell, an induced pluripotent embryonic stem (iES) cell, or an adult cell.

5. The method of claim 4 wherein the adult cell is a carcinoma, somatic, or fibroblast cell.

6. The method of claim 1, wherein the cell is an ES cell and the nuclear proteins are ES cell specific transcriptional factor or factors.

7. The method of claim 6 wherein the ES cell specific transcriptional factors are Oct4, Sox2, c-Myc and Klf4.

8. A method for inducing one or more isolated differentiated cell or cells into pluripotent stem (iPS) cell or cells, comprising:

infecting the isolated differentiated cell or cells with a *Pseudomonas* bacteria deletion mutant lacking genes encoding ExoS, ExoT, and ExoY proteins, said deletion mutant comprising a plasmid or plasmids comprising nucleic acid sequences encoding one or more fusion proteins, wherein each nucleic acid sequence comprises a nucleic acid sequence encoding a stem cell specific transcriptional factor fused to a nucleic acid sequence encoding the N-terminus of an ExoS protein or a nucleic acid sequence encoding a signal sequence from an ExoS protein, and the nucleic acid further comprises a nucleic acid sequence encoding a nuclear localization sequence between the nucleic acid sequence encoding the N-terminus of an ExoS protein or a nucleic acid sequence encoding a signal sequence from an ExoS protein and the nucleic acid sequence encoding the transcriptional factors, wherein the transcription factors are Oct4, Sox2, c-Myc, and Klf4;

incubating the isolated infected cell or cells under embryonic stem (ES) cell culture conditions such that Oct-4, Sox-2, c-Myc and Klf-4 proteins are introduced into the cell or cells to form a population of iPS cells.

9. The method of claim 1, wherein the *Pseudomonas* deletion mutant is PAKΔSTY, PAKΔSTYΔpopN, PAK-JΔSTY, or PAK-JΔSTYΔpopN.

10. The method of claim 1, wherein the signal sequence from ExoS protein is ExoS17, ExoS54, ExoS96, or ExoS234.

11. The method of claim 1, wherein the signal sequence from ExoS protein is ExoS54.

12. The method of claim 8, wherein the *Pseudomonas* deletion mutant is PAKΔSTY, PAKΔSTYΔpopN, PAK-JΔSTY, or PAK-JΔSTYΔpopN.

13. The method of claim 8, wherein the signal sequence from ExoS protein is ExoS17, ExoS54, ExoS96, or ExoS234.

14. The method of claim 8, wherein the signal sequence from ExoS protein is ExoS54.

15. A method of delivering one or more nuclear proteins into one or more isolated cells, comprising:

incubating the cell or cells with a *Pseudomonas aerogenosa* bacteria deletion mutant lacking genes encoding ExoS, ExoT, and ExoY proteins, said deletion mutant comprising a plasmid or plasmids comprising nucleic acid sequences encoding one or more fusion proteins, wherein each nucleic acid sequence comprises a nucleic acid sequence encoding a nuclear protein fused to a nucleic acid sequence encoding the N-terminus of an ExoS protein or a nucleic acid sequence encoding a signal sequence from an ExoS protein, and the nucleic acid further comprises a nucleic acid sequence encoding a nuclear localization sequence between the nucleic acid sequence encoding the N-terminus of an ExoS protein or a nucleic acid sequence encoding a signal sequence from an ExoS protein and the nucleic acid sequence encoding the nuclear protein;

and incubating the isolated infected cell or cells for a period of time sufficient to deliver the one or more nuclear proteins into said cell or cells.

* * * * *

UNITED STATES PATENT AND TRADEMARK OFFICE
CERTIFICATE OF CORRECTION

PATENT NO. : 8,617,888 B2
APPLICATION NO. : 12/842448
DATED : December 31, 2013
INVENTOR(S) : Shouguang Jin et al.

It is certified that error appears in the above-identified patent and that said Letters Patent is hereby corrected as shown below:

In the Specification

Column 4,
Line 1, "in a various" should read --in various--.
Line 5, "environment The" should read --environment. The--.

Column 6,
Line 38, "contain a foxed" should read --contain a floxed--.
Line 60, "contain a foxed" should read --contain a floxed--.

Column 7,
Line 3, "contain a foxed" should read --contain a floxed--.

Column 11,
Line 22, "foxed SV40" should read --floxed SV40--.

Column 12,
Line 58, "recombination is may not" should read --recombination may not--.
Line 66, "cytotoxicity Currently," should read --cytotoxicity. Currently,--.

Column 14,
Line 43, "400 PBS" should read --40µl PBS--.

Column 16,
Line 30, "or BglII" should read --or *Bgl*II--.
Line 32, "or BglII" should read --or *Bgl*II--.
Line 34, "or BglII" should read --or *Bgl*II--.
Line 36, "or BglII" should read --or *Bgl*II--.

Signed and Sealed this
Tenth Day of March, 2015

Michelle K. Lee
*Deputy Director of the United States Patent and Trademark Office*